US008748150B2

(12) United States Patent
Padmanabhan et al.

(10) Patent No.: US 8,748,150 B2
(45) Date of Patent: *Jun. 10, 2014

(54) PHAGE DERIVED ANTIMICROBIAL ACTIVITIES

(75) Inventors: Sriram Padmanabhan, Bangalore (IN); Vivek Daniel Paul, Bangalore (IN); R. Sanjeev Saravanan, Bangalore (IN); Bharathi Sriram, Bangalore (IN)

(73) Assignee: GangaGen, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,750

(22) Filed: May 21, 2012

(65) Prior Publication Data

US 2012/0237491 A1    Sep. 20, 2012

Related U.S. Application Data

(62) Division of application No. 12/299,601, filed as application No. PCT/US2007/010972 on May 4, 2007, now Pat. No. 8,202,516.

(60) Provisional application No. 60/797,885, filed on May 5, 2006, provisional application No. 60/909,340, filed on Mar. 30, 2007.

(51) Int. Cl.
*C12N 9/24* (2006.01)
*C12N 9/36* (2006.01)

(52) U.S. Cl.
USPC .................. 435/206; 424/94.61; 435/200

(58) Field of Classification Search
None
See application file for complete search history.

(56) References Cited

U.S. PATENT DOCUMENTS

2005/0208038 A1 * 9/2005 Fischetti et al. ........... 424/94.63
2005/0214773 A1   9/2005 Edwards et al.

FOREIGN PATENT DOCUMENTS

WO    WO 97/08553 A1    3/1997
WO    WO 2008/001342 A1    1/2008

OTHER PUBLICATIONS

Baba, Tadashi et al.; "Target cell specificity of a bacteriocin molecule: a C-terminal signal directs lysostaphin to the cell wall of *Staphylococcus aureus*"; 1996, *The EMBO Journal*, vol. 15, No. 18, pp. 4789-4797.

Bateman, Alex et al.; "The CHAP domain: a large family of amidases including GSP amidase and peptidoglycan hydrolases"; 2003, *Trends in Biochemical Sciences*, vol. 28, No. 5, pp. 234-237.
Borysowski, Jan et al.; "Bacteriophage Endolysins as a Novel Class of Antibacterial Agents"; 2006, Experimental Biology and Medicine, vol. 231, No. 4, pp. 366-377.
Croux, C. et al.; "Interchange of functional domains switches enzyme specificity: construction of a chimeric pneumococcal-clostridial cell wall lytic enzyme"; 1993, *Molecular Microbiology*, vol. 9, No. 5, pp. 1019-1025.
Donovan, David M. et al.; "Peptidoglycan Hydrolase Fusions Maintain Their Parental Specificities"; 2006, *Applied and Environmental Microbiology*, vol. 72, No. 4, pp. 2988-2996.
Kenny, J.G., et al., "Bacteriophage Tuc2009 Encodes a Tail-Associated Cell Wall-Degrading Activity", Jun. 2004) *J. Bacteriology* 186(11): 2480-3491.
Kwan, Tony et al.; "The complete genomes and proteomes of 27 *Staphylococcus aureus* bacteriophages"; 2005, *PNAS*, vol. 102, No. 14, pp. 5174-5179.
Lopez, Rubens et al.; "Enzymes for anti-infective therapy: phage lysins"; 2004, *Drug Discovery Today*, vol. 1, No. 4, pp. 469-474.
Sans, Jesus M. et al.; "Construction of a multifunctional pneumococcal murein hydrolase by module assembly"; 1996, *Eur. J. Biochem.*, vol. 235, pp. 601-605.
Sheehan, Michelle M. et al.; "Analysis of the catalytic domain of the lysine of the lactococcal bacteriophage Tuc2009 by chimeric gene assembling"; 1996, *FEMS Microbiology Letters*, vol. 140, pp. 23-28.
Takae, M. et al.,"Phage P68 Virion-Associated Protein 17 Displays Activity Against Clinical Isolates of *Staphylococcus aureus*", Jul. 2005 *Antimicrobial Agents Chemotherapy*, 49(7): 2934-2940.
UniProt., Database accession No. Q6Y7R1, 2004, 1 page.
UniProt, Database accession No. Q4ZA05, 2005, 1 page.
UniProt, Database accession No. Q4Z9D9, 2005, 1 page.
UniProt, Database accession No. Q8CNS6, 2003, 1 page.
Ramadurai et al.; "Molecular cloning, sequencing, and expression of lytM, a unique autolytic gene of *Staphylococcus aureus*"; *J. Bacteriol.*; 179(11):3625-3631 (1997).
Supplementary European Search Report from EP 07794592.1, dated Aug. 5, 2010.
Office Action from CN Appl. No. 200780016254.0, dated Jun. 24, 2011.
Office Action from JP Appl. No. 2009-509770, dated Nov. 14, 2012.
Office Action from CA Appl. No. 2,651,125, dated Jun. 27, 2013.
Takáč, M. et al.,"Phage P68 Virion-Associated Protein 17 Displays Activity Against Clinical Isolates of *Staphylococcus aureus*", Jul. 2005 *Antimicrobial Agents Chemotherapy*, 49(7): 2934-2940.

* cited by examiner

*Primary Examiner* — Rebecca Prouty
(74) *Attorney, Agent, or Firm* — Kilpatrick Townsend & Stockton LLP

(57) ABSTRACT

The present invention provides methods and compositions to reduce growth of microbial colonies, including infections, and includes therapeutic compositions, methods for treatment of infections, and methods for identifying additional such compositions.

15 Claims, 2 Drawing Sheets

TAME Candidate Genes in Current Staphylococcal Phages

| Phage | Morphology/group | Genome nt | # Proteins | TAME CD | TAME CD | TAME CD | TAME genbank entry |
|---|---|---|---|---|---|---|---|
| Staphylococcus phage 11 | Siphoviridae | 43604 | 53 | CHAP | LYZ2 |  | >gi|29028612|ref|NP_803302.1| cell wall hydrolase [Staphylococcus aureus phage phi 11] |
| Staphylococcus phage 187 | Siphoviridae | 39620 | 77 | CHAP | LYZ2 |  | >gi|66395217|ref|YP_239513.1| ORF102 [Staphylococcus phage 187] |
| Staphylococcus phage 2638A | Siphoviridae | 41318 | 57 | LT_GEWL | Peptidase_M23 |  | >gi|66395451|ref|YP_239811.1| ORF01 [Staphylococcus phage 2638A] |
| Staphylococcus phage 29 | Siphoviridae, phage 53 sensu lato | 42802 | 75 | CHAP | LYZ2 |  | >gi|62636612|gb|AAX91723.1| ORF04 [Bacteriophage 29] |
| Staphylococcus phage 37 | Siphoviridae | 43681 | 77 | CHAP | LYZ2 |  | >gi|62636156|gb|AAX91267.1| ORF04 [Bacteriophage 37] |
| Staphylococcus phage 3A | Siphoviridae | 43095 | 67 | LT_GEWL |  |  | >gi|213597767|gb|AAM49603.1|AF513855_3 phi12 tail fiber protein-like protein [Staphylococcus aureus bacteriophage phi 3A] |
| Staphylococcus phage 42E | Siphoviridae | 45861 | 79 | LT_GEWL |  |  | >gi|62636002|gb|AAX91113.1| ORF01 [Bacteriophage 42e] |
| Staphylococcus phage 44AHJD | Podophage Phi29-like viruses | 16784 | 21 |  | CHAP* |  | >gi|29378355|gb|AAO33864.1| unknown [Staphylococcus phage 44AHJD] |
| Staphylococcus phage 47 | Siphoviridae, phage 53 sensu lato | 44777 | 72 | LT_GEWL |  |  | >gi|66395657|ref|YP_240016.1| ORF01 [Staphylococcus phage 47] |
| Staphylococcus phage 52A | Siphoviridae, phage 53 sensu lato | 41690 | 65 | CHAP | LYZ2 |  | >gi|62636687|gb|AAX91798.1| ORF04 [Bacteriophage 52A] |
| Staphylococcus phage 53 | Siphoviridae, phage 53 sensu lato | 43683 | 79 | CHAP | LYZ2 |  | >gi|66395374|ref|YP_239671.1| ORF04 [Staphylococcus phage 53] |
| Staphylococcus phage 55 | Siphoviridae | 41902 | 77 | CHAP | LYZ2 |  | >gi|62636535|gb|AAX91646.1| ORF04 [Bacteriophage 55] |
| Staphylococcus phage 66 | Podophage Phi29-like viruses | 18199 | 27 | CHAP | CHAP |  | >gi|66395191|ref|YP_239474.1| ORF01 [Staphylococcus phage 66] |
| Staphylococcus phage 69 | Siphoviridae, phage 53 sensu lato | 42732 | 76 | CHAP | LYZ2 |  | >gi|66395297|ref|YP_239591.1| ORF04 [Staphylococcus phage 69] |
| Staphylococcus phage 71 | Siphoviridae, phage 53 sensu lato | 43114 | 72 | CHAP | LYZ2 |  | >gi|62636463|gb|AAX91574.1| ORF04 [Bacteriophage 71] |
| Staphylococcus phage 77 | Siphoviridae | 41708 | 69 | LT_GEWL | Peptidase_M23 |  | >gi|41189516|ref|NP_958615.1| 77ORF01 [Bacteriophage 77] |
| Staphylococcus phage 85 | Siphoviridae, phage 53 sensu lato | 44283 | 78 | CHAP | LYZ2 |  | >gi|62635803|gb|AAX90914.1| ORF04 [Bacteriophage 85] |
| Staphylococcus phage 88 | Siphoviridae, phage 53 sensu lato | 43231 | 72 | CHAP | LYZ2 |  | >gi|66396337|ref|YP_240695.1| ORF04 [Staphylococcus phage 88] |
| Staphylococcus phage 92 | Siphoviridae, phage 53 sensu lato | 42431 | 74 | CHAP | LYZ2 |  | >gi|66396410|ref|YP_240769.1| ORF04 [Staphylococcus phage 92] |
| Staphylococcus phage 96 | Siphoviridae, phage 53 sensu lato | 43576 | 79 | CHAP | LYZ2 |  | >gi|66395889|ref|YP_240255.1| ORF04 [Staphylococcus phage 96] |
| Staphylococcus phage EW | Siphoviridae | 45286 | 77 | CHAP | LYZ2 |  | >gi|66395810|ref|YP_240176.1| ORF03 [Staphylococcus phage EW] |
| Staphylococcus phage G1 | Myoviridae | 138715 | 214 | CHAP | CHAP |  | >gi|66394954|ref|YP_240321.1| ORF05 [Staphylococcus phage G1] |
| Staphylococcus phage K | Myoviridae | 127395 | 115 | CHAP | CHAP |  | >gi|48896445|ref|YP_024486.1| hypothetical protein KgORF56 [Staphylococcus phage K] |

| Phage | Family | Size | # | Domain1 | Domain2 | Note | Accession |
|---|---|---|---|---|---|---|---|
| Staphylococcus phage P68 | Podophage Phi29-like viruses | 18227 | 22 | | CHAP* | • | >gi|29956754|ref|NP_817327.1| unknown [Staphylococcus aureus phage phiP68] |
| Staphylococcus phage PH15 | Siphoviridae | 44041 | 68 | | LYZ2 | • | >gi|112790093|gb|ABI26613.2| hydrolase [Staphylococcus phage PH15] |
| Staphylococcus phage phi 12 | Siphoviridae | 44970 | 49 | CHAP | Peptidase M23 | • | >gi|29028657|ref|NP_803346.1| tail fiber protein [Staphylococcus aureus phage phi 12] |
| Staphylococcus phage phi 13 | Siphoviridae | 42722 | 49 | LT_GEWL | Peptidase M23 | • | >gi|29028706|ref|NP_803396.1| tail length tape measure protein [Staphylococcus aureus phage phi 13] |
| Staphylococcus phage phiETA | Siphoviridae | 43081 | 66 | CHAP | LYZ2 | • | >gi|17426289|ref|NP_510955.1| similar to phage phi187 cell hydrolase Ply187 [Bacteriophage phi ETA] |
| Staphylococcus phage phiETA2 | Siphoviridae | 43265 | 69 | CHAP | LYZ2 | • | >gi|122891778|ref|YP_001004324.1| cell wall hydrolase [Staphylococcus phage phiETA2] |
| Staphylococcus phage phiETA3 | Siphoviridae | 43282 | 68 | CHAP | LYZ2 | • | >gi|121309326|dbj|BAF43947.1| cell wall hydrolase [Bacteriophage phi ETA3] |
| Staphylococcus phage phiN315 | Siphoviridae | 44082 | 65 | LT_GEWL | Peptidase M23 | SLT | >gi|30043943|ref|NP_835564.1| hypothetical protein SA1766 [Staphylococcus phage phiN315] |
| Staphylococcus phage phiNM | Siphoviridae | 43128 | 64 | CHAP | LYZ2 | • | >gi|118430784|ref|YP_874009.1| cell wall hydrolase [Staphylococcus aureus phage phiNM] |
| Staphylococcus phage phiNM3 | Siphoviridae | 44061 | 63 | LT_GEWL | Peptidase M23 | • | >gi|118725105|ref|YP_908841.1| phage tail tape measure protein [Staphylococcus aureus phage phiNM3] |
| Staphylococcus phage phiPVL108 | Siphoviridae | 44857 | 59 | LT_GEWL | Peptidase M23 | • | >gi|119443702|ref|YP_919840.1| tail length tape measure protein2 [Staphylococcus bacteriophage phiPVL108] |
| Staphylococcus phage phiSLT | Siphoviridae | 42942 | 61 | LT_GEWL | Peptidase M23 | • | >gi|46917483|dbj|BAB21743.2| unnamed protein product [Staphylococcus aureus temperate phage phiSLT] |
| Staphylococcus phage Twort | Myoviridae | 130706 | 195 | CHAP | | • | >gi|66391262|ref|YP_238556.1| ORF007 [Staphylococcus phage Twort] |
| Staphylococcus phage X2 | Siphoviridae, phage 53 sensu lato | 43440 | 77 | CHAP | LYZ2 | | >gi|26368699|gb|AAX92010.1| ORF005 [Bacteriophage X2] |
| Staphylococcus prophage phiPV83 | Siphoviridae | 45636 | 65 | Peptidase M23 | | | >gi|9653722|ref|NP_061640.1| phi PVL ORF15 and 16 homologue [Staphylococcus aureus prophage phiPV83] |
| Staphylococcus phage CNPH82 | Siphoviridae | 43420 | 65 | CHAP | LYZ2 | LytD | >gi|119953703|ref|YP_950623.1| amidase [Staphylococcus phage CNPH82] |
| Staphylococcus phage ROSA | | 43155 | 74 | CHAP | LYZ2 | | gi|263638|gb|AAX91500.1|ORF004| [Bacteriophage ROSA] |
| Staphylococcus phage 80alpha | | | | CHAP | LYZ2 | | gi|03958695|gb|ABF71638.1|Staphylococcus phage 80alpha |
| Staphylococcus aureus phage phi 12 | Siphoviridae | 4970 | 49 | LT_GEWL | Peptidase M23 | | gi|29028657|NP_803346.1|tail fiber protein [Staphylococcus aureus phage phi 12] |
| Staphylococcus prophage L54a | | | | LT_GEWL | Peptidase M23 | | gi|57632568|YP_185211.1|Staphylococcus prophage L54a | note: "sensu lato" = "in the wider sense", this is the new NCBI term to designate phage groups (as in T4 sensu lato = T2, T4, T6 etc)
CHAP* = These are CDs detected by homology with the known CHAP-containing ORFs; i.e., phage 66 ORF04

(cont.)

SEQUENCE LISTING

<160> NUMBER OF SEQ ID NOS: 13

<210> SEQ ID NO 1
<211> LENGTH: 808
<212> TYPE: PRT

<213> ORGANISM: Staphylococcus phage K
<220> FEATURE:
<223> OTHER INFORMATION: hypothetical protein KgORF56, ORF56
<220> FEATURE:
<221> NAME/KEY: DOMAIN
<222> LOCATION: (629)..(690)
<223> OTHER INFORMATION: ORF56 binding fragment, binding domain of ORF56
<220> FEATURE:
<221> NAME/KEY: PEPTIDE
<222> LOCATION: (629)..(808)
<223> OTHER INFORMATION: ORF56 19 KDa fragment
<220> FEATURE:
<221> NAME/KEY: PEPTIDE
<222> LOCATION: (669)..(808)
<223> OTHER INFORMATION: ORF56 16 KDa fragment
<220> FEATURE:
<221> NAME/KEY: DOMAIN
<222> LOCATION: (691)..(808)
<223> OTHER INFORMATION: ORF56 13 KDa fragment, Cysteine-Histidine dependent Aminohydrolase/Peptidase (CHAP) domain

<400> SEQUENCE: 1

Met Arg Arg Ile Arg Arg Pro Lys Val Arg Ile Glu Ile Val Thr Asp
 1               5                  10                  15

Asp Asn Thr Phe Thr Leu Arg Phe Glu Asp Thr Arg Asp Tyr Asn Gly
             20                  25                  30

Asp Glu Phe Gly Ala Lys Leu Leu Gly Phe Gln Thr Lys Asn Ser Met
         35                  40                  45

Glu Asp Asp Ser Ser Val Phe Gln Ile Asn Met Ala Gly Asp Thr Tyr
     50                  55                  60

Trp Asp Lys Leu Val Met Ala Asn Asp Ile Ile Arg Ile Phe Ile Thr
 65                  70                  75                  80

Pro Asn Asp Asp Pro Asn Asp Lys Glu Gly Lys Gln Glu Arg Leu Ile
                 85                  90                  95

Gln Val Gly Met Val Ser Gln Val Ser Lys Val Gly Ser Tyr Gly Asn
            100                 105                 110

Asp Gln Thr Gln Phe Arg Ile Thr Gly Gln Ser Phe Val Lys Pro Phe
        115                 120                 125

Met Lys Phe Gly Leu Gly Val Ile Gln Glu Val Gln Ala Val Leu Pro
    130                 135                 140

Glu Val Gly Trp Leu Ile Asp Gly Asp Gly Asp Asn Glu Val Lys Phe
145                 150                 155                 160

Thr Gly Ser Ser Ala His Glu Val Met Thr Gly Ile Ile Arg Arg Phe
                165                 170                 175

Ile Pro Tyr Met Lys Tyr Asn Tyr Thr Glu Lys Thr Tyr Asn Thr Ile
            180                 185                 190

Asp Asn Tyr Leu Asp Tyr Asp Leu Ser Ser Trp Asp Glu Phe Glu
        195                 200                 205

Lys Leu Thr Glu Val Ser Ala Phe Thr Asn Phe Asp Gly Ser Leu Lys
    210                 215                 220

Gln Leu Met Asp Met Val Thr Ala Arg Pro Phe Asn Glu Leu Phe Phe
225                 230                 235                 240

Lys Asn Ser Glu Lys Thr Pro Gly Lys Ala Gln Leu Val Leu Arg Lys
                245                 250                 255

Thr Pro Phe Asn Pro Thr Glu Trp Arg Ala Leu Asp Met Ile Lys Val
            260                 265                 270

Pro Thr Glu Asp Phe Ile Glu Glu Asp Val Gly Lys Ser Asp Val Glu
        275                 280                 285

Thr Tyr Ser Ile Phe Thr Ala Thr Pro Ala Gly Met Leu Lys Glu Leu
    290                 295                 300

```
-continued

Asn Gly Asp Val Phe Ser Lys Pro Gln Phe His Pro Glu Leu Thr Asp
305                 310                 315                 320

Arg Tyr Gly Tyr Thr Lys Phe Glu Val Glu Asn Ile Tyr Leu Ser Thr
                325                 330                 335

Lys Ser Gly Ser Ala Thr Glu Asp Ser Asp Ser Ser Gly Asp Asp Asn
            340                 345                 350

Gly Thr Glu Arg Gly Thr Tyr Ser Lys Ile Met Lys Asp Leu Ser Asn
        355                 360                 365

Tyr Gly Arg Asp Asn Ile Ser Lys Gly Ile Asp Lys Tyr Thr Ser Lys
    370                 375                 380

Leu Ser Ser Lys Tyr Lys Asn Leu Lys Lys Ala Gln Ala Lys Lys Ile
385                 390                 395                 400

Ile Glu Lys Phe Val Lys Glu Gly Lys Val Thr Glu Lys Glu Tyr Glu
                405                 410                 415

Lys Ile Thr Gly Asn Lys Val Asp Asp Glu Leu Thr Ser Asp Asn Arg
            420                 425                 430

Pro Lys Leu Thr Lys Asp Lys Leu Lys Ser Ile Leu Lys Glu Lys Phe
        435                 440                 445

Lys Thr Gln Asp Phe Asn Asn Ser Lys Lys Lys Lys Ala Lys
    450                 455                 460

Thr Asp Ala Leu Lys Glu Leu Thr Thr Lys Tyr Arg Phe Gly Asn Lys
465                 470                 475                 480

Thr His Ala Thr Thr Leu Leu Asp Glu Tyr Ile Lys Tyr Lys Gly Glu
                485                 490                 495

Pro Pro Asn Asp Glu Ala Phe Asp Lys Tyr Leu Lys Ala Ile Glu Gly
            500                 505                 510

Val Ser Asn Val Ala Thr Asp Thr Gly Ser Asp Ala Ser Asp Ser Pro
        515                 520                 525

Leu Val Met Phe Ser Arg Met Leu Phe Asn Trp Tyr His Gly Asn Pro
530                 535                 540

Asn Phe Tyr Ala Gly Asp Ile Ile Val Leu Gly Asp Pro Lys Tyr Asp
545                 550                 555                 560

Leu Gly Lys Arg Leu Phe Ile Glu Asp Lys Gln Arg Gly Asp Thr Trp
                565                 570                 575

Glu Phe Tyr Ile Glu Ser Val Glu His Lys Phe Asp Tyr Lys Gln Gly
            580                 585                 590

Tyr Tyr Thr Thr Val Gly Val Thr Arg Gly Leu Lys Asp Ala Ile Leu
        595                 600                 605

Glu Asp Gly Lys Gly Ser Pro His Arg Phe Ala Gly Leu Trp Asn Gln
610                 615                 620

Ser Ser Asp Phe Met Gly Gly Leu Met Gly Glu Asp Thr Ser Lys Glu
625                 630                 635                 640

Leu Lys Glu Lys Gly Val Ala Glu Lys Gln Ser Ser Gly Asp Lys Asp
                645                 650                 655

Gly Gly Ser Asp Ser Gly Gly Ala Gln Asp Gly Gly Ser Leu Asp Ser
            660                 665                 670

Leu Lys Lys Tyr Asn Gly Lys Leu Pro Lys His Asp Pro Ser Phe Val
        675                 680                 685

Gln Pro Gly Asn Arg His Tyr Lys Tyr Gln Cys Thr Trp Tyr Ala Tyr
690                 695                 700

Asn Arg Arg Gly Gln Leu Gly Ile Pro Val Pro Leu Trp Gly Asp Ala
705                 710                 715                 720

Ala Asp Trp Ile Gly Gly Ala Lys Gly Ala Gly Tyr Gly Val Gly Arg
                725                 730                 735
```

```
Thr Pro Lys Gln Gly Ala Cys Val Ile Trp Gln Arg Gly Val Gln Gly
            740                 745                 750

Gly Ser Pro Gln Tyr Gly His Val Ala Phe Val Glu Lys Val Leu Asp
        755                 760                 765

Gly Gly Lys Lys Ile Phe Ile Ser Glu His Asn Tyr Ala Thr Pro Asn
    770                 775                 780

Gly Tyr Gly Thr Arg Thr Ile Asp Met Ser Ser Ala Ile Gly Lys Asn
785                 790                 795                 800

Ala Gln Phe Ile Tyr Asp Lys Lys
                805

<210> SEQ ID NO 2
<211> LENGTH: 3060
<212> TYPE: DNA
<213> ORGANISM: Staphylococcus phage K
<220> FEATURE:
<223> OTHER INFORMATION: segment of Staphylococcus phage K virion genome
      containing ORF56, locus tag KgORF56
<220> FEATURE:
<221> NAME/KEY: CDS
<222> LOCATION: (165)..(2591)
<223> OTHER INFORMATION: hypothetical protein KgORF56, ORF56, ORF from
      58185 to 60611 within Staphylococcus phage K virion genome

<400> SEQUENCE: 2
ctggagacat tatcggagga agaattagag aagttctaga tagtaacatg gatatctttg      60
caaatgaaca taagagaagt tattagtaat tttgtattga cacaagagta gtatcatagt     120
atactactct tatacatata aaaataaaaa ggaagtatgt gtatatgcgt agaataagaa     180
gacctaaggt aagaatagaa atagttacag atgataatac atttacattg agatttgaag     240
atacacgaga ctataatggt gatgagtttg gagctaaact tttaggattc caaactaaaa     300
actctatgga agatgatagt tcagttttcc aaataaatat ggcaggagat acttattggg     360
ataagctagt tatggctaat gatatcataa gaatatttat tacacctaat gatgacccta     420
acgataaaga aggaaaacaa gaacgactta tccaggtagg tatggtttct caagtatcaa     480
aagtaggtag ttacggtaat gaccaaactc aatttagaat aacaggtcaa tcttttgtaa     540
aaccttttat gaaatttgga ttaggcgtta ttcaggaagt tcaagctgta ttacctgaag     600
taggttggct tattgatggt gatggagata tgaagtaaa atttactggt agctcagctc     660
atgaagtaat gactggtatt atacgtagat ttataccttat tatgaaatat aactatactg     720
aaaaaacata taatacaatt gataactatc ttgattatga tgatttaagt agttgggatg     780
agtttgaaaa acttacagaa gtttcagcct ttactaattt tgatgggtca ttaaaacagt     840
taatggatat ggtaacagct agacctttta atgagttatt cttcaaaaat tcagaaaaaa     900
cacctggaaa ggctcaactt gtattaagaa agaccccttt taatcctact gagtggagag     960
ctttagatat gattaaagta cctactgagg attttataga agaggatgta ggtaaaagtg    1020
atgtagagac atattctata tttacagcaa cacctgcagg tatgttgaaa gagcttaacg    1080
gtgatgtatt ttctaaacca caattccacc ctgaattaac tgatagatat ggttatacta    1140
aatttgaagt agaaaatatt tatcttagta caaaatcagg ttcagctact gaggattcag    1200
attcttcagg tgatgataat ggcacagaac gaggaactta ttctaaaatt atgaaagatt    1260
taagtaacta tggaagagat aatatatcta aaggtataga taagtataca agtaaattat    1320
cttcaaaata taaaaactta aaaaaagccc aagctaaaaa aattatagag aagtttgtta    1380
aagaaggaaa agtaacagaa aaagaatatg aaaaaataac aggtaataag gtagatgatg    1440
```

```
aattaacatc agataacaga ccgaagttga caaaagataa attaagagt atactaaaag    1500 agaagtttaa aacacaagat gatttaata attctaagaa aaagaaaaaa gctaagacag    1560
atgcacttaa agaattgaca actaaatatc gttttggtaa taaaacacat gctacaactt    1620
tattagatga atatattaaa tataaaggag agccacctaa cgatgaggct tttgataaat    1680
atcttaaagc tattgaaggt gttagtaatg tagctacaga cacaggttca gatgcaagtg    1740 ataqcccttt agttatgttt tctagaatgc tatttaattg gtatcatggt aaccctaact    1800
tctatgcagg agatattatt gttttaggag accctaagta tgacctaggt aaaagattat    1860
ttattgaaga taagcaacga ggagacactt gggagttcta tattgaatct gtagaacata    1920
aattcgatta taaacagggg tattatacaa ctgtaggagt aactagaggt ttaaaagacg    1980
ctattctaga agatggtaaa ggtagtccgc atagatttgc aggattatgg aatcaatcat    2040
cagacttcat gggaggtctt atgggtgaag atacttctaa agaacttaaa gaaaaggtg    2100 tagcagagaa acaaagtagt ggagataaag atggtggttc tgatagtggt ggagctcaag    2160
atggtggctc tttagattca cttaaaaaat ataacggcaa acttcctaag catgacccaa    2220
gttttgttca acctggtaac cgacattata agtatcagtg tacatggtat gcttataata    2280
gaagaggtca attaggcata cctgtgcctt tatgggggga cgccgccgac tggataggtg    2340
gtgctaaagg agcaggttat ggtgtaggta gaacacctaa acaaggtgct tgtgttatat    2400
ggcaaagagg agttcaagga ggtagcccac aatatggtca cgtagcgttt gtagagaaag    2460
tattagatgg aggtaaaaaa atatttatct ctgaacataa ctatgctacc cctaatggat    2520
atggtactag aacgatagat atgagttcag ccataggtaa gaatgcacaa ttcatttacg    2580
ataagaaata aaggaggata gtctatggca acagataaag aagctaaaga tgttattgat    2640
aaatttatag acaatgtatt taattttgat gtacttacaa agaaagaat aaaagaaaaa    2700 gatgaagaaa ttaaaaaaat aactacagat gatatgtatg aaaaggttgt gtatatacga    2760
ccttatgttg gagtaataca aagccttaac cctcagcatg ttcagtatga atcatttct    2820 aataatggtt atgatataga ggcagaatta agtttcagga aagtaagtta tttagttgat    2880
aaagggtcta tacctacaga ttctttatct actttaacag ttcatttagt agaacgaaat    2940
caagaactat taatagatta ctttgatgag atacaagatg tgttgtatgg agaatatatg    3000
gaagaagaat atgtatttga tgaagatgta ccattaagta cgatactagc attagactta    3060
```

<210> SEQ ID NO 3
<211> LENGTH: 632
<212> TYPE: PRT
<213> ORGANISM: Staphylococcus aureus phage phi11
<220> FEATURE:
<223> OTHER INFORMATION: Staphylococcus aureus phage phi11 cell wall hydrolase, ORF 49, phi11 49
<220> FEATURE:
<221> NAME/KEY: DOMAIN
<222> LOCATION: (27)..(151)
<223> OTHER INFORMATION: Cysteine-Histidine dependent Aminohydrolase/Peptidase (CHAP) domain

<400> SEQUENCE: 3

Met Gly Leu Pro Asn Pro Lys Asn Arg Lys Pro Thr Ala Ser Glu Val
1               5                   10                  15

Val Glu Trp Ala Leu Tyr Ile Ala Lys Asn Lys Ile Ala Ile Asp Val
            20                  25                  30

Pro Gly Ser Gly Met Gly Ala Gln Cys Trp Asp Leu Pro Asn Tyr Leu
        35                  40                  45

Leu Asp Lys Tyr Trp Gly Phe Arg Thr Trp Gly Asn Ala Asp Ala Met

```
            50                  55                  60
Ala Gln Lys Ser Asn Tyr Arg Gly Arg Asp Phe Lys Ile Ile Arg Asn
 65                  70                  75                  80

Thr Lys Asp Phe Val Pro Gln Pro Gly Asp Trp Gly Val Trp Thr Gly
                 85                  90                  95

Gly Trp Ala Gly His Val Asn Ile Val Val Gly Pro Cys Thr Lys Asp
            100                 105                 110

Tyr Trp Tyr Gly Val Asp Gln Asn Trp Tyr Thr Asn Asn Ala Thr Gly
        115                 120                 125

Ser Pro Pro Tyr Lys Ile Lys His Ser Tyr His Asp Gly Pro Gly Gly
130                 135                 140

Gly Val Lys Tyr Phe Val Arg Pro Pro Tyr His Pro Asp Lys Thr Thr
145                 150                 155                 160

Pro Ala Pro Lys Pro Glu Asp Asp Ser Asp Asp Asn Glu Lys Asn Asn
                165                 170                 175

Lys Lys Val Pro Ile Trp Lys Asp Val Thr Thr Ile Lys Tyr Thr Ile
            180                 185                 190

Ser Ser Gln Glu Val Asn Tyr Pro Glu Tyr Ile Tyr His Phe Ile Val
        195                 200                 205

Glu Gly Asn Arg Arg Leu Glu Lys Pro Lys Gly Ile Met Ile Arg Asn
210                 215                 220

Ala Gln Thr Met Ser Ser Val Glu Ser Leu Tyr Asn Ser Arg Lys Lys
225                 230                 235                 240

Tyr Lys Gln Asp Val Glu Tyr Pro His Phe Tyr Val Asp Arg His Asn
                245                 250                 255

Ile Trp Ala Pro Arg Arg Ala Val Phe Glu Val Pro Asn Glu Pro Asp
            260                 265                 270

Tyr Ile Val Ile Asp Val Cys Glu Asp Tyr Ser Ala Ser Lys Asn Glu
        275                 280                 285

Phe Ile Phe Asn Glu Ile His Ala Met Val Val Ala Val Asp Met Met
290                 295                 300

Ala Lys Tyr Glu Ile Pro Leu Ser Ile Glu Asn Leu Lys Val Asp Asp
305                 310                 315                 320

Ser Ile Trp Arg Ser Met Leu Glu His Val Asn Trp Asn Met Ile Asp
                325                 330                 335

Asn Gly Val Pro Pro Lys Asp Lys Tyr Glu Ala Leu Glu Lys Ala Leu
            340                 345                 350

Leu Asn Ile Phe Lys Asn Arg Glu Lys Leu Leu Asn Ser Ile Thr Lys
        355                 360                 365

Pro Thr Val Thr Lys Ser Arg Ile Lys Val Met Val Asp Asn Lys Asn
370                 375                 380

Ala Asp Ile Ala Asn Val Arg Asp Ser Ser Pro Thr Ala Asn Asn Gly
385                 390                 395                 400

Ser Ala Ser Lys Gln Pro Gln Ile Ile Thr Glu Thr Ser Pro Tyr Thr
                405                 410                 415

Phe Lys Gln Ala Leu Asp Lys Gln Met Ala Arg Gly Asn Pro Lys Lys
            420                 425                 430

Ser Asn Ala Trp Gly Trp Ala Asn Ala Thr Arg Ala Gln Thr Ser Ser
        435                 440                 445

Ala Met Asn Val Lys Arg Ile Trp Glu Ser Asn Thr Gln Cys Tyr Gln
450                 455                 460

Met Leu Asn Leu Gly Lys Tyr Gln Gly Val Ser Val Ser Ala Leu Asn
465                 470                 475                 480
```

```
Lys Ile Leu Lys Gly Lys Gly Thr Leu Asn Asn Gln Gly Lys Ala Phe
                485                 490                 495

Ala Glu Ala Cys Lys Lys His Asn Ile Asn Glu Ile Tyr Leu Ile Ala
            500                 505                 510

His Ala Phe Leu Glu Ser Gly Tyr Gly Thr Ser Asn Phe Ala Asn Gly
        515                 520                 525

Lys Asp Gly Val Tyr Asn Tyr Phe Gly Ile Gly Ala Tyr Asp Asn Asn
    530                 535                 540

Pro Asn Tyr Ala Met Thr Phe Ala Arg Asn Lys Gly Trp Thr Ser Pro
545                 550                 555                 560

Ala Lys Ala Ile Met Gly Gly Ala Ser Phe Val Arg Lys Asp Tyr Ile
                565                 570                 575

Asn Lys Gly Gln Asn Thr Leu Tyr Arg Ile Arg Trp Asn Pro Lys Asn
            580                 585                 590

Pro Ala Thr His Gln Tyr Ala Thr Ala Ile Glu Trp Cys Gln His Gln
        595                 600                 605

Ala Ser Thr Ile Ala Lys Leu Tyr Lys Gln Ile Gly Leu Lys Gly Ile
    610                 615                 620

Tyr Phe Thr Arg Asp Lys Tyr Lys
625                 630

<210> SEQ ID NO 4
<211> LENGTH: 240
<212> TYPE: PRT
<213> ORGANISM: Artificial Sequence
<220> FEATURE:
<223> OTHER INFORMATION: Description of Artificial Sequence:Construct 1,
      fusion construct Met-(16 KDa ORF56 catalytic fragment)-Leu-Glu-
      (lysostaphin binding fragment), Staphylococcus simulans
      lysostaphin binding domain (BD) fused to C-terminus of 16 KDa
      ORF56, chimera 128
<220> FEATURE:
<221> NAME/KEY: DOMAIN
<222> LOCATION: (2)..(141)
<223> OTHER INFORMATION: phage K 16 KDa ORF56 catalytic fragment
<220> FEATURE:
<221> NAME/KEY: DOMAIN
<222> LOCATION: (144)..(240)
<223> OTHER INFORMATION: lysostaphin binding domain (BD), lysostaphin
      binding fragment

<400> SEQUENCE: 4

Met Ser Leu Asp Ser Leu Lys Lys Tyr Asn Gly Lys Leu Pro Lys His
1               5                   10                  15

Asp Pro Ser Phe Val Gln Pro Gly Asn Arg His Tyr Lys Tyr Gln Cys
            20                  25                  30

Thr Trp Tyr Ala Tyr Asn Arg Arg Gly Gln Leu Gly Ile Pro Val Pro
        35                  40                  45

Leu Trp Gly Asp Ala Ala Asp Trp Ile Gly Gly Ala Lys Gly Ala Gly
    50                  55                  60

Tyr Gly Val Gly Arg Thr Pro Lys Gln Gly Ala Cys Val Ile Trp Gln
65                  70                  75                  80

Arg Gly Val Gln Gly Gly Ser Pro Gln Tyr Gly His Val Ala Phe Val
                85                  90                  95

Glu Lys Val Leu Asp Gly Gly Lys Lys Ile Phe Ile Ser Glu His Asn
            100                 105                 110

Tyr Ala Thr Pro Asn Gly Tyr Gly Thr Arg Thr Ile Asp Met Ser Ser
        115                 120                 125

Ala Ile Gly Lys Asn Ala Gln Phe Ile Tyr Asp Lys Lys Leu Glu Thr
    130                 135                 140
```

```
Pro Asn Thr Gly Trp Lys Thr Asn Lys Tyr Gly Thr Leu Tyr Lys Ser
145                 150                 155                 160

Glu Ser Ala Ser Phe Thr Pro Asn Thr Asp Ile Ile Thr Arg Thr Thr
                165                 170                 175

Gly Pro Phe Arg Ser Met Pro Gln Ser Gly Val Leu Lys Ala Gly Gln
            180                 185                 190

Thr Ile His Tyr Asp Glu Val Met Lys Gln Asp Gly His Val Trp Val
        195                 200                 205

Gly Tyr Thr Gly Asn Ser Gly Gln Arg Ile Tyr Leu Pro Val Arg Thr
    210                 215                 220

Trp Asn Lys Ser Thr Asn Thr Leu Gly Val Leu Trp Gly Thr Ile Lys
225                 230                 235                 240

<210> SEQ ID NO 5

<400> SEQUENCE: 5

000

<210> SEQ ID NO 6
<211> LENGTH: 280
<212> TYPE: PRT
<213> ORGANISM: Artificial Sequence
<220> FEATURE:
<223> OTHER INFORMATION: Description of Artificial Sequence:Construct 2,
      fusion construct (19 KDa ORF56 catalytic fragment)-Leu-Glu-
      (lysostaphin binding fragment), Staphylococcus simulans
      lysostaphin binding domain (BD) fused to C-terminus of 19 KDa
      ORF56
<220> FEATURE:
<221> NAME/KEY: DOMAIN
<222> LOCATION: (1)..(181)
<223> OTHER INFORMATION: phage K 19 KDa ORF56 catalytic fragment
<220> FEATURE:
<221> NAME/KEY: DOMAIN
<222> LOCATION: (184)..(280)
<223> OTHER INFORMATION: lysostaphin binding domain (BD), lysostaphin
      binding fragment

<400> SEQUENCE: 6

Met Gly Gly Leu Met Met Gly Glu Asp Thr Ser Lys Glu Leu Lys Glu
1               5                   10                  15

Lys Gly Val Ala Glu Lys Gln Ser Ser Gly Asp Lys Asp Gly Ser
                20                  25                  30

Asp Ser Gly Gly Ala Gln Asp Gly Gly Ser Leu Asp Ser Leu Lys Lys
            35                  40                  45

Tyr Asn Gly Lys Leu Pro Lys His Asp Pro Ser Phe Val Gln Pro Gly
    50                  55                  60

Asn Arg His Tyr Lys Tyr Gln Cys Thr Trp Tyr Ala Tyr Asn Arg Arg
65                  70                  75                  80

Gly Gln Leu Gly Ile Pro Val Pro Leu Trp Gly Asp Ala Ala Asp Trp
                85                  90                  95

Ile Gly Gly Ala Lys Gly Ala Gly Tyr Gly Val Gly Arg Thr Pro Lys
            100                 105                 110

Gln Gly Ala Cys Val Ile Trp Gln Arg Gly Val Gln Gly Gly Ser Pro
        115                 120                 125

Gln Tyr Gly His Val Ala Phe Val Glu Lys Val Leu Asp Gly Gly Lys
    130                 135                 140

Lys Ile Phe Ile Ser Glu His Asn Tyr Ala Thr Pro Asn Gly Tyr Gly
145                 150                 155                 160

Thr Arg Thr Ile Asp Met Ser Ser Ala Ile Gly Lys Asn Ala Gln Phe
                165                 170                 175
```

Ile Tyr Asp Lys Lys Leu Glu Thr Pro Asn Thr Gly Trp Lys Thr Asn
            180                 185                 190

Lys Tyr Gly Thr Leu Tyr Lys Ser Glu Ser Ala Ser Phe Thr Pro Asn
            195                 200                 205

Thr Asp Ile Ile Thr Arg Thr Thr Gly Pro Phe Arg Ser Met Pro Gln
            210                 215                 220

Ser Gly Val Leu Lys Ala Gly Gln Thr Ile His Tyr Asp Glu Val Met
225                 230                 235                 240

Lys Gln Asp Gly His Val Trp Val Gly Tyr Thr Gly Asn Ser Gly Gln
            245                 250                 255

Arg Ile Tyr Leu Pro Val Arg Thr Trp Asn Lys Ser Thr Asn Thr Leu
            260                 265                 270

Gly Val Leu Trp Gly Thr Ile Lys
            275                 280

<210> SEQ ID NO 7
<211> LENGTH: 217
<212> TYPE: PRT
<213> ORGANISM: Artificial Sequence
<220> FEATURE:
<223> OTHER INFORMATION: Description of Artificial Sequence:Construct 3,
      fusion construct (13 KDa ORF56 catalytic fragment)-Leu-Glu-
      (lysostaphin binding fragment), Staphylococcus simulans
      lysostaphin binding domain (BD) fused to C-terminus of 13 KDa
      ORF56 CHAP domain
<220> FEATURE:
<221> NAME/KEY: DOMAIN
<222> LOCATION: (1)..(118)
<223> OTHER INFORMATION: phage K 13 KDa ORF56 catalytic fragment,
      Cysteine-Histidine dependent Aminohydrolase/Peptidase (CHAP)
      domain
<220> FEATURE:
<221> NAME/KEY: DOMAIN
<222> LOCATION: (121)..(217)
<223> OTHER INFORMATION: lysostaphin binding domain (BD), lysostaphin
      binding fragment

<400> SEQUENCE: 7

Gly Asn Arg His Tyr Lys Tyr Gln Cys Thr Trp Tyr Ala Tyr Asn Arg
1               5                   10                  15

Arg Gly Gln Leu Gly Ile Pro Val Pro Leu Trp Gly Asp Ala Ala Asp
            20                  25                  30

Trp Ile Gly Gly Ala Lys Gly Ala Gly Tyr Gly Val Gly Arg Thr Pro
        35                  40                  45

Lys Gln Gly Ala Cys Val Ile Trp Gln Arg Gly Val Gln Gly Gly Ser
    50                  55                  60

Pro Gln Tyr Gly His Val Ala Phe Val Glu Lys Val Leu Asp Gly Gly
65                  70                  75                  80

Lys Lys Ile Phe Ile Ser Glu His Asn Tyr Ala Thr Pro Asn Gly Tyr
            85                  90                  95

Gly Thr Arg Thr Ile Asp Met Ser Ser Ala Ile Gly Lys Asn Ala Gln
            100                 105                 110

Phe Ile Tyr Asp Lys Lys Leu Glu Thr Pro Asn Thr Gly Trp Lys Thr
            115                 120                 125

Asn Lys Tyr Gly Thr Leu Tyr Lys Ser Glu Ser Ala Ser Phe Thr Pro
            130                 135                 140

Asn Thr Asp Ile Ile Thr Arg Thr Thr Gly Pro Phe Arg Ser Met Pro
145                 150                 155                 160

Gln Ser Gly Val Leu Lys Ala Gly Gln Thr Ile His Tyr Asp Glu Val
            165                 170                 175

```
Met Lys Gln Asp Gly His Val Trp Val Gly Tyr Thr Gly Asn Ser Gly
            180                 185                 190

Gln Arg Ile Tyr Leu Pro Val Arg Thr Trp Asn Lys Ser Thr Asn Thr
            195                 200                 205

Leu Gly Val Leu Trp Gly Thr Ile Lys
            210                 215

<210> SEQ ID NO 8
<211> LENGTH: 257
<212> TYPE: PRT
<213> ORGANISM: Artificial Sequence
<220> FEATURE:
<223> OTHER INFORMATION: Description of Artificial Sequence:Construct 4,
      fusion construct (16 KDa ORF56 catalytic fragment)-Leu-Glu-(L54a
      amidase binding fragment), phage L54a binding domain (BD) fused to
      C-terminus of 16 KDa ORF56
<220> FEATURE:
<221> NAME/KEY: DOMAIN
<222> LOCATION: (7)..(146)
<223> OTHER INFORMATION: phage K 16 KDa ORF56 catalytic fragment
<220> FEATURE:
<221> NAME/KEY: DOMAIN
<222> LOCATION: (149)..(257)
<223> OTHER INFORMATION: prophage L54a amidase binding domain (BD), L54a
      amidase binding fragment

<400> SEQUENCE: 8

Met Ala Gln Asp Gly Gly Ser Leu Asp Ser Leu Lys Lys Tyr Asn Gly
 1               5                  10                  15

Lys Leu Pro Lys His Asp Pro Ser Phe Val Gln Pro Gly Asn Arg His
             20                  25                  30

Tyr Lys Tyr Gln Cys Thr Trp Tyr Ala Tyr Asn Arg Arg Gly Gln Leu
         35                  40                  45

Gly Ile Pro Val Pro Leu Trp Gly Asp Ala Ala Asp Trp Ile Gly Gly
     50                  55                  60

Ala Lys Gly Ala Gly Tyr Gly Val Gly Arg Thr Pro Lys Gln Gly Ala
 65                  70                  75                  80

Cys Val Ile Trp Gln Arg Gly Val Gln Gly Ser Pro Gln Tyr Gly
                 85                  90                  95

His Val Ala Phe Val Glu Lys Val Leu Asp Gly Gly Lys Lys Ile Phe
            100                 105                 110

Ile Ser Glu His Asn Tyr Ala Thr Pro Asn Gly Tyr Gly Thr Arg Thr
            115                 120                 125

Ile Asp Met Ser Ser Ala Ile Gly Lys Asn Ala Gln Phe Ile Tyr Asp
            130                 135                 140

Lys Lys Leu Glu Lys Thr Ser Ala Lys Asn Gln Lys Asn Pro Pro Val
145                 150                 155                 160

Pro Ala Gly Tyr Thr Leu Asp Lys Asn Asn Val Pro Tyr Lys Lys Glu
                165                 170                 175

Gln Gly Asn Tyr Thr Val Ala Asn Val Lys Gly Asn Asn Val Arg Asp
            180                 185                 190

Gly Tyr Ser Thr Asn Ser Arg Ile Thr Gly Val Leu Pro Asn Asn Thr
            195                 200                 205

Thr Ile Thr Tyr Asp Gly Ala Tyr Cys Ile Asn Gly Tyr Arg Trp Ile
    210                 215                 220

Thr Tyr Ile Ala Asn Ser Gly Gln Arg Arg Tyr Ile Ala Thr Gly Glu
225                 230                 235                 240

Val Asp Lys Ala Gly Asn Arg Ile Ser Ser Phe Gly Lys Phe Ser Thr
                245                 250                 255

Ile
```

```
<210> SEQ ID NO 9
<211> LENGTH: 199
<212> TYPE: PRT
<213> ORGANISM: Artificial Sequence
<220> FEATURE:
<223> OTHER INFORMATION: Description of Artificial Sequence:Construct 5,
      fusion construct (LytM peptidase catalytic fragment)-Leu-Glu-
      (lysostaphin binding fragment), LytM peptidase domain fused to
      C-terminus of Staphylococcus simulans lysostaphin binding domain
      (BD)
<220> FEATURE:
<221> NAME/KEY: DOMAIN
<222> LOCATION: (1)..(100)
<223> OTHER INFORMATION: Staphylococcus aureus peptidoglycan hydrolase
      (LytM) peptidase domain, LytM peptidase catalytic
      fragment
<220> FEATURE:
<221> NAME/KEY: DOMAIN
<222> LOCATION: (103)..(199)
<223> OTHER INFORMATION: lysostaphin binding domain (BD), lysostaphin
      binding fragment

<400> SEQUENCE: 9

Met Pro Glu Asn Ser Pro Val Tyr Ser Leu Thr Asp Gly Thr Val Val
 1               5                  10                  15

Gln Ala Gly Trp Ser Asn Tyr Gly Gly Gly Asn Gln Val Thr Ile Lys
            20                  25                  30

Glu Ala Asn Ser Asn Asn Tyr Gln Trp Tyr Met His Asn Asn Arg Leu
        35                  40                  45

Thr Val Ser Ala Gly Asp Lys Val Lys Ala Gly Asp Gln Ile Ala Tyr
    50                  55                  60

Ser Gly Ser Thr Gly Asn Ser Thr Ala Pro His Val His Phe Gln Arg
65                  70                  75                  80

Met Ser Gly Gly Ile Gly Asn Gln Tyr Ala Val Asp Pro Thr Ser Tyr
                85                  90                  95

Leu Gln Ser Arg Leu Glu Thr Pro Asn Thr Gly Trp Lys Thr Asn Lys
            100                 105                 110

Tyr Gly Thr Leu Tyr Lys Ser Glu Ser Ala Ser Phe Thr Pro Asn Thr
        115                 120                 125

Asp Ile Ile Thr Arg Thr Thr Gly Pro Phe Arg Ser Met Pro Gln Ser
    130                 135                 140

Gly Val Leu Lys Ala Gly Gln Thr Ile His Tyr Asp Glu Val Met Lys
145                 150                 155                 160

Gln Asp Gly His Val Trp Val Gly Tyr Thr Gly Asn Ser Gly Gln Arg
                165                 170                 175

Ile Tyr Leu Pro Val Arg Thr Trp Asn Lys Ser Thr Asn Thr Leu Gly
            180                 185                 190

Val Leu Trp Gly Thr Ile Lys
        195

<210> SEQ ID NO 10
<211> LENGTH: 211
<212> TYPE: PRT
<213> ORGANISM: Artificial Sequence
<220> FEATURE:
<223> OTHER INFORMATION: Description of Artificial Sequence:Construct 6,
      fusion construct Met-(lysostaphin catalytic fragment)-(ORF56
      binding fragment), Staphylococcus simulans lysostaphin catalytic
      domain fused to ORF56 binding domain
<220> FEATURE:
<221> NAME/KEY: DOMAIN
<222> LOCATION: (2)..(148)
<223> OTHER INFORMATION: lysostaphin catalytic fragment, lysostaphin
      catalytic domain, catalytic (lys-lys cleavage) fragment
```

```
<220> FEATURE:
<221> NAME/KEY: DOMAIN
<222> LOCATION: (149)..(211)
<223> OTHER INFORMATION: ORF56 binding domain, ORF56 binding fragment

<400> SEQUENCE: 10

Met Ala Ala Thr His Glu His Ser Ala Gln Trp Leu Asn Asn Tyr Lys
 1               5                  10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Lys Ala
    130                 135                 140

Gly Gly Thr Val Met Gly Gly Leu Met Met Gly Glu Asp Thr Ser Lys
145                 150                 155                 160

Glu Leu Lys Glu Lys Gly Val Ala Glu Lys Gln Ser Ser Gly Asp Lys
                165                 170                 175

Asp Gly Gly Ser Asp Ser Gly Gly Ala Gln Asp Gly Gly Ser Leu Asp
            180                 185                 190

Ser Leu Lys Lys Tyr Asn Gly Lys Leu Pro Lys His Asp Pro Ser Phe
        195                 200                 205

Val Gln Pro
    210

<210> SEQ ID NO 11
<211> LENGTH: 340
<212> TYPE: PRT
<213> ORGANISM: Artificial Sequence
<220> FEATURE:
<223> OTHER INFORMATION: Description of Artificial Sequence:Construct 7,
      fusion construct (LytM peptidase catalytic fragment)-16 KDa ORF56
      catalytic fragment)-Leu-Glu-(lysostaphin binding fragment), LytM
      peptidase-16 KDa ORF56-lysostaphin binding domain (BD)
<220> FEATURE:
<221> NAME/KEY: DOMAIN
<222> LOCATION: (1)..(100)
<223> OTHER INFORMATION: Staphylococcus aureus peptidoglycan hydrolase
      (LytM) peptidase domain, LytM peptidase catalytic fragment
<220> FEATURE:
<221> NAME/KEY: DOMAIN
<222> LOCATION: (102)..(241)
<223> OTHER INFORMATION: phage K 16 KDa ORF56 catalytic fragment
<220> FEATURE:
<221> NAME/KEY: DOMAIN
<222> LOCATION: (244)..(340)
<223> OTHER INFORMATION: lysostaphin binding domain (BD), lysostaphin
      binding fragment

<400> SEQUENCE: 11

Met Pro Glu Asn Ser Pro Val Tyr Ser Leu Thr Asp Gly Thr Val Val
 1               5                  10                  15

Gln Ala Gly Trp Ser Asn Tyr Gly Gly Gly Asn Gln Val Thr Ile Lys
```

```
                20                  25                  30
        Glu Ala Asn Ser Asn Asn Tyr Gln Trp Tyr Met His Asn Asn Arg Leu
                    35                  40                  45

Thr Val Ser Ala Gly Asp Lys Val Lys Ala Gly Asp Gln Ile Ala Tyr
         50                  55                  60

Ser Gly Ser Thr Gly Asn Ser Thr Ala Pro His Val His Phe Gln Arg
         65                  70                  75                  80

Met Ser Gly Gly Ile Gly Asn Gln Tyr Ala Val Asp Pro Thr Ser Tyr
                        85                  90                  95

Leu Gln Ser Arg Met Ser Leu Asp Ser Leu Lys Lys Tyr Asn Gly Lys
                    100                 105                 110

Leu Pro Lys His Asp Pro Ser Phe Val Gln Pro Gly Asn Arg His Tyr
                115                 120                 125

Lys Tyr Gln Cys Thr Trp Tyr Ala Tyr Asn Arg Arg Gly Gln Leu Gly
        130                 135                 140

Ile Pro Val Pro Leu Trp Gly Asp Ala Ala Asp Trp Ile Gly Gly Ala
        145                 150                 155                 160

Lys Gly Ala Gly Tyr Gly Val Gly Arg Thr Pro Lys Gln Gly Ala Cys
                        165                 170                 175

Val Ile Trp Gln Arg Gly Val Gln Gly Ser Pro Gln Tyr Gly His
                    180                 185                 190

Val Ala Phe Val Glu Lys Val Leu Asp Gly Gly Lys Lys Ile Phe Ile
                195                 200                 205

Ser Glu His Asn Tyr Ala Thr Pro Asn Gly Tyr Gly Thr Arg Thr Ile
            210                 215                 220

Asp Met Ser Ser Ala Ile Gly Lys Asn Ala Gln Phe Ile Tyr Asp Lys
        225                 230                 235                 240

Lys Leu Glu Thr Pro Asn Thr Gly Trp Lys Thr Asn Lys Tyr Gly Thr
                        245                 250                 255

Leu Tyr Lys Ser Glu Ser Ala Ser Phe Thr Pro Asn Thr Asp Ile Ile
                    260                 265                 270

Thr Arg Thr Thr Gly Pro Phe Arg Ser Met Pro Gln Ser Gly Val Leu
                275                 280                 285

Lys Ala Gly Gln Thr Ile His Tyr Asp Glu Val Met Lys Gln Asp Gly
        290                 295                 300

His Val Trp Val Gly Tyr Thr Gly Asn Ser Gly Gln Arg Ile Tyr Leu
        305                 310                 315                 320

Pro Val Arg Thr Trp Asn Lys Ser Thr Asn Thr Leu Gly Val Leu Trp
                        325                 330                 335

Gly Thr Ile Lys
                    340

<210> SEQ ID NO 12
<211> LENGTH: 243
<212> TYPE: PRT
<213> ORGANISM: Artificial Sequence
<220> FEATURE:
<223> OTHER INFORMATION: Description of Artificial Sequence:Construct 8,
      fusion construct Met-(16KDa ORF56 catalytic fragment)-Leu-Glu-
      (phi11 amidase binding fragment), C-terminus of 16 KDa ORF56 fused
      to Staphylococcus aureus phage phi11 amidase binding domain (BD)
<220> FEATURE:
<221> NAME/KEY: DOMAIN
<222> LOCATION: (2)..(141)
<223> OTHER INFORMATION: phage K 16 KDa ORF56 catalytic fragment
<220> FEATURE:
<221> NAME/KEY: DOMAIN
<222> LOCATION: (144)..(243)
<223> OTHER INFORMATION: Staphylococcus aureus phage phi11 amidase
```

-continued binding domain (BD), phi11 amidase binding fragment

<400> SEQUENCE: 12

Met Ser Leu Asp Ser Leu Lys Lys Tyr Asn Gly Lys Leu Pro Lys His
1               5                   10                  15

Asp Pro Ser Phe Val Gln Pro Gly Asn Arg His Tyr Lys Tyr Gln Cys
                20                  25                  30

Thr Trp Tyr Ala Tyr Asn Arg Arg Gly Gln Leu Gly Ile Pro Val Pro
            35                  40                  45

Leu Trp Gly Asp Ala Ala Asp Trp Ile Gly Gly Ala Lys Gly Ala Gly
    50                  55                  60

Tyr Gly Val Gly Arg Thr Pro Lys Gln Gly Ala Cys Val Ile Trp Gln
65                  70                  75                  80

Arg Gly Val Gln Gly Gly Ser Pro Gln Tyr Gly His Val Ala Phe Val
                85                  90                  95

Glu Lys Val Leu Asp Gly Gly Lys Lys Ile Phe Ile Ser Glu His Asn
            100                 105                 110

Tyr Ala Thr Pro Asn Gly Tyr Gly Thr Arg Thr Ile Asp Met Ser Ser
            115                 120                 125

Ala Ile Gly Lys Asn Ala Gln Phe Ile Tyr Asp Lys Lys Leu Glu Pro
    130                 135                 140

Val Ala Ser Ala Trp Lys Arg Asn Lys Tyr Gly Thr Tyr Tyr Met Glu
145                 150                 155                 160

Glu Ser Ala Arg Phe Thr Asn Gly Asn Gln Pro Ile Thr Val Arg Lys
                165                 170                 175

Val Gly Pro Phe Leu Ser Cys Pro Val Gly Tyr Gln Phe Gln Pro Gly
            180                 185                 190

Gly Tyr Cys Asp Tyr Thr Glu Val Met Leu Gln Asp Gly His Val Trp
    195                 200                 205

Val Gly Tyr Thr Trp Glu Gly Gln Arg Tyr Tyr Leu Pro Ile Arg Thr
    210                 215                 220

Trp Asn Gly Ser Ala Pro Pro Asn Gln Ile Leu Gly Asp Leu Trp Gly
225                 230                 235                 240

Glu Ile Ser

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:six adjacent
      histidines, polyhistidine epitope tag, poly His, purification tag

<400> SEQUENCE: 13

His His His His His His
1               5

PHAGE DERIVED ANTIMICROBIAL ACTIVITIES

CROSS-REFERENCES TO RELATED APPLICATIONS

This application claims priority to U.S. application Ser. No. 12/299,601, now U.S. Pat. No. 8,202,516, filed Mar. 27, 2009 as a U.S. National Phase Application under 35 U.S.C. §371 of International Application No. PCT/US2007/010972, filed on May 4, 2007, which claims the benefit of U.S. Provisional Application No. 60/797,885, filed May 5, 2006 and U.S. Provisional Application No. 60/909,340, filed Mar. 30, 2007; the disclosures of which are herein incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -11-3.txt, created on May 21, 2012, 40,960 bytes, machine format IBM-PC, MS-Windows operating system, is hereby incorporated by reference in its entirety for all purposes.

FIELD OF INVENTION

The present invention provides methods and compositions to reduce growth of microbial colonies, including infections, and includes therapeutic compositions, methods for treatment of infections, and methods for identifying additional such compositions.

BACKGROUND OF THE INVENTION

Bacteria are ubiquitous, and are found in virtually all habitable environments. They are common and diverse ecologically, and find unusual and common niches for survival. They are present throughout the environment, and are present in soil, dust, water, and on virtually all surfaces. Many are normal and beneficial strains, which provide a synergistic relationship with hosts. Others are not so beneficial, or cause problems along with benefits.

Pathogenic bacteria can cause infectious diseases in humans, in other animals, and also in plants. Some bacteria can only make particular hosts ill; others cause trouble in a number of hosts, depending on the host specificity of the bacteria. Diseases caused by bacteria are almost as diverse as the bacteria themselves and include food poisoning, tooth decay, *anthrax*, general infectious diseases, and even certain forms of cancer. These are typically the subject of the field of clinical microbiology.

Bacteria are killed in nature by bacteria-specific viruses, e.g., bacteriophage, or phage. Many phages found in nature belong to the group Caudovirales, or "tailed" phages. These viruses invariably have a single double-stranded DNA genome packaged into a proteinaceous capsid. The phage consists of three fundamental structures: the head; which in general has icosahedral symmetry, a tail structure emanating from one vertex of the icosahedral head, and 4-6 tail fibers attached to some part of the tail. It should be noted that the Order Caudoviralescontains three general morphotypes: Podoviridae (podophage), Myoviridae (myophage), and Siphoviridae (siphophage). Strictly speaking, the podophage do not have a morphogenetically separate "tail"; that is, the tail-like structure is actually assembled as part of head or capsid assembly. In the myophage and siphophage, there are separate morphogenesis pathways for heads, tails and tail fibers; all three are eventually joined together to form complete infectious virions. In podophage, there is a head pathway and a tail fiber pathway. From a functional perspective, however, the tail like structure of podophage serves the same function as the genuine tails of the other two morphotypes.

Phages kill cells by infecting, replicating, and then lysing the host cell, releasing multiple progeny virions in the process. Certain phage-derived elements are also capable of killing cells. For example, many *Pseudomonas* strains produce pyocins, proteinaceous components that kill other *Pseudomonas* strains. In general, the term "bacteriocin" is used to describe compounds produced by bacteria that kill other bacteria; bacteriocins of a wide-variety of chemical structure, from small molecules to polypeptides, are known. However, many of the pyocins were found to be "headless tails", i.e., phage tails produced without heads or DNA. These tail-like bacteriocins kill bacteria by adsorbing to them and causing a fatal lesion in the cell envelope, although, lacking DNA, there is no replication or host lysis. Since the original discovery of the pyocins in *Pseudomonas*, similar tail-like bacteriocins have been identified in a wide variety of other bacteria, including both Gram-negative and Gram-positive species. See, e.g., Nakayama, et al. (2000) *Mol. Microbiol.* 38:213-31; Traub, et al. (1996) *Zentralbl. Bakteriol.* 284:124-35; Ito, et al. (1986) *J. Virol.* 59:103-111; Rocourt (1986) *Zentralbl. Bakteriol. Mikrobiol. Hyg.* 261:12-28; Shinomiya (1984) *J. Virol.* 49:310-14; Ishii, et al. (1965) *J. Mol. Biol.* 13:428-431; Daw and Falkiner (1996) *Micron.* 27:467-479; Strauch, et al. (2001) *Appl. Environ. Microbiol.* 67:5635-5642; and Abdelhamid, et al. (2002) *Appl. Environ. Microbiol.* 68:5704-5710. In addition, other bactericidal elements derived from phage have been described. For example, Caudovirales encode an endolysin as part of the host cell lysis functions. These enzymes degrade the host cell wall from within, leading to lysis and release of the progeny virions. Phage endolysins added exogenously to cultures or suspensions of bacteria have been shown to be capable of lysing and killing a number of Gram-positive bacteria. See, e.g., Fischetti, et al. (2005) US Pat App 20050208038 describing use of phage endolysins to kill bacteria and Takac and Blasi (2005) *Antimicrob. Agents and Chemother.* 49:2934-2940.

Certain bacteria are normally innocuous, but become pathogenic upon presentation of the appropriate opportunity, or become problematic upon introduction to an abnormal site or situation. Persons lacking effective immune systems are most vulnerable, and certain bacteria use susceptible weak hosts to provide a temporary environment to proliferate and disperse throughout the population.

Statistically, infectious diseases are a major medical problem. See, e.g., Watstein and Jovanovic (2003) *Statistical Handbook on Infectious Diseases* Greenwood, ISBN: 1573563757. In the U.S., some 40-70K deaths result from bloodstream nosocomial (hospital derived) infections each year.

Antibiotics have revolutionized clinical medicine over the last half century. Since the original discovery of antibiotic phenomenon, the mechanism of action and development of this class of remarkable therapeutic entities has made enormous progress. See, e.g., Therrien and Levesque (2000) *FEMS Microbial Rev.* 24:251-62; Durgess (1999) *Chest* 115(3 Suppl):19S-23S; Medeiros (1997) *Clin. Infect. Dis.* 24(Suppl 1):S19-45; Jones (1996) *Am. J. Med.* 100(6A):3S-12S; Ford and Hait (1993) *Cytotechnology* 12:171-212; and Liu (1992) *Compr Ther.* 18:35-42. Antibiotics had about $32B worldwide sales in 2002.

The widespread appearance of antibiotic-resistant bacteria has emphasized the vulnerability of current antimicrobial treatments to bacterial adaptation. See, e.g., Walsh (1992) *Antibiotics: Actions, Origins, Resistance* Amer. Soc. Microbiol., ISBN: 1555812546; Cunha (1992) *Antibiotic Essentials* Physicians Press, ISBN: 1890114413; Amyes (2003) *Magic Bullets, Lost Horizons: The Rise and Fall of Antibiotics* Taylor & Francis, ISBN: 0415272033; Axelsen (2001) *Essentials of Antimicrobial Pharmacology: A Guide to Fundamentals for Practice* Humana Press, ISBN: 0896038424; and Mainous and Pomeroy (eds. 2001) *Management of Antimicrobials in Infectious Diseases: Impact of Antibiotic Resistance* Humana Press, ISBN: 0896038211. However, many classical antibiotics require rapid replication or growth of the target bacteria to be effective.

Thus, improved methods for decreasing target bacterial growth or survival or limiting bacterial pathogenicity will find great utility. This utility may be applicable to environmental, local, topical, or particularly in vivo colonization. The present invention addresses these and other significant problems.

BRIEF SUMMARY OF THE INVENTION

The present invention is based, in part, upon the discovery that phage-encoded cell wall degrading activities, e.g., murein-degrading (commonly designated "muralytic") enzymes, which are typically the core of the phage lysis functions to exit the host cell, are also found as structural components of the phage virion and assist entry of the phage into a host cell. These activities, designated here as TAMES (tail-associated murein-degrading enzymes), have intrinsic bactericidal activity, irrespective of the phage replicative pathway. Each phage particle of all three morphotypes is thought to have a TAME associated with the tail structure or, in the case of the podophage, associated as a minor component of the head or capsid. It is thought that local degradation of the cell wall facilitates the DNA injection process. The invention describes a particular phage TAME, ORF56, the product of orf56 of the staphylococcal myovirus K. In particular, purified ORF56, heretofore not recognized as a "lytic" agent, is found to have bactericidal activity. Moreover, bactericidal polypeptides derived from ORF56 by truncation have been identified. Bactericidal activity can be screened for from similar or related sources, e.g., sources of similar structures and domains from various evolutionarily diverse sources, to find additional bactericidal activities which possess advantageous properties. Such sources may also be starting points for mutagenesis and screening for additional advantageous properties, e.g., stability, bactericidal efficiency, size, substrate specificity, and such. Most importantly, robust bactericidal activity, significantly (e.g., orders of magnitude, or multiple factors) more efficient than found for the purified TAME ORF56 or its truncation derivatives, is found for a chimera consisting of the murein-degrading catalytic domain of ORF56 and the non-catalytic cell-wall binding domain (CBD) of the lytic Staphylococcal bacteriocin, lysostaphin. These TAME-CBD chimeras are much more efficient in terms of bactericidal activity than the purified TAME. Moreover, the TAME-CBD chimeric protein is shown to persist in an efficacious state (e.g. retains enzymatic stability), in terms of bactericidal activities, in a number of useful formulation mixtures. Purified proteins based thereon, and nucleic acid sequences encoding such are provided, along with antibodies thereto. Methods for using said compositions are provided, including methods to reduce the growth or presence of the target bacteria.

The present invention provides a method of killing a bacterium susceptible to a cell wall degrading activity, said method comprising introducing to the environment of said bacterium a composition selected from: a) a purified TAME component of a phage tail or a tail-like bacteriocin; b) a cell wall degrading portion of the phage K ORF56 TAME or the presumptive TAME of phage phi11, ORF49; c) a substantially pure polypeptide comprising a cell wall degrading polypeptide of phage K ORF56 or phage phi11 ORF49; or d) a pharmaceutical composition consisting essentially of the TAME homologs, or fragment thereof, from other phages or tail-like bacteriocin. Examples of sources include a group consisting of: YP_238566 (ORF007 (*Staphylococcus* phage Twort)), YP_406405 (gp29 (*Listeria* bacteriophage P100)), NP_765044 (secretory antigen SsaA-like protein (*Staphylococcus epidermidis* ATCC 12228)), YP_164769 (orf134 (*Lactobacillus plantarum* bacteriophage LP65)), YP_492702 (transfer complex protein TraG (*Staphylococcus aureus* subsp. *aureus* USA300)), AAA71958 (putative (*Staphylococcus aureus*)), NP_765786 (N-acetylmuramoyl-L-alanine amidase (*Staphylococcus epidermidis* ATCC 12228)), YP_189676 (secretory antigen precursor SsaA-related protein (*Staphylococcus epidermidis* RP62A)), YP_189814 (N-acetylmuramoyl-L-alanine amidase (*Staphylococcus epidermidis* RP62A)), and other designated sources further described below. Another source is the phage phi11 ORF49, a putative cell wall hydrolase (NP_803302; GeneID:1258067).

The invention further provides methods, as described, wherein: the bacterium belongs to genus *Staphylococcus*; and specifically is *S. aureus, S. epidermidis* and other staphylococci of clinical significance; the environment is in vivo or on a mucosal or other organ surface or on a medical device or implant; the introducing is topical, systemic, parenteral, or by inhalation; another antimicrobial treatment is used, including an antibiotic or phage-derived product; or said bactericidal activity has a broad target specificity across multiple bacterial strains and/or across multiple bacterial species.

Various methods are provided for screening for a phage-derived bactericidal activity on a target bacterium, said method comprising: fragmenting a source phage into separable structural fragments; determining which fragments retain binding affinity for said target bacterium; and testing said fragments for bactericidal activity; thereby identifying structures possessing said bactericidal activity. This also includes embodiments wherein the data from the method is communicated into a US jurisdiction. In certain embodiments, the target bacterium is a Gram-positive bacterium or the bactericidal activity is a muralytic activity.

More methods are provided, including one for generating variant bactericidal activities, the method comprising mutagenizing a gene encoding a polypeptide characterized as exhibiting cell wall degrading activity; and screening for variants with modified bacteriocidal activity. Communicating the data from such a method would also be encompassed. Other methods include that described, but evaluating for modified bactericidal activity, e.g., different substrate turnover number; or a change in sensitivity of enzymatic properties to reaction conditions, including temperature, salt, pH, hydration, or the like.

Treatment methods are provided, including one of treating a bacterial infection in an animal, the method comprising administering to said animal one or more bactericidal polypeptides, wherein at least two of said polypeptides are derived from different cell wall degrading genes; the bactericidal polypeptides have broad target bactericidal activity; the bactericidal proteins are "lytic" when applied to the exterior of the cell; or the bactericidal activity is murein-degrading, or muralytic, which includes proteins with murein glycosidase (including glucosaminidase and muraminidase), transglycosylase, lysozyme, amidase or endopeptidase activities.

The present invention provides an ORF56 or ORF49 polypeptide that has bactericidal activity against a target bacterium and that, at a minimum includes an amino acid sequence with at least 80%, 90% or 95% identity to amino acid residues 620-808 of SEQ ID NO: 1 or residues 481-618 of SEQ ID NO: 3. In one embodiment, the ORF56 protein includes the exact sequence of amino acid residues 620-808 of SEQ ID NO: 1 or the ORF49 protein includes the exact sequence of amino acid residues 481-618 of SEQ ID NO: 3. In a further embodiment, the invention provides a composition that consists essentially of an ORF56 polypeptide that has bactericidal activity against a target bacterium and that, at a minimum, includes an amino acid sequence with at least 80%, 90%, or 95% identity to amino acid residues 620-808 of SEQ ID NO: 1 or residues 481-618 of SEQ ID NO: 3.

In one embodiment, the invention provides a composition, e.g., a pharmaceutical composition, a diagnostic reagent, or a bactericidal composition, that includes an ORF56 or ORF49 polypeptide that has bactericidal activity against a target bacterium and that includes an amino acid sequence with at least 80%, 90%, or 95% identity to, at a minimum, amino acid residues 620-808 of SEQ ID NO: 1 or residues 481-618 of SEQ ID NO: 3. The composition can include at least one other protein with bactericidal activity, e.g., a p16 protein from phage p68 or a Pal-type "lytic enzyme". The composition can also include other ingredients with bacteristatic or bactericidal activity, e.g., an antibiotic.

The disclosed ORF56 or ORF49 polypeptides can be used to prevent growth of a target bacterium that is a *Staphylococcus* species, and in particular a methicillin-resistant *Staphylococcus* species. In another embodiment, the target bacterium is a slowly replicating bacterial species, e.g., a bacterium that has a doubling time between one and seventy-two hours, or more, e.g., about 2, 4, 8, 12, 20, 30, 40, or 50 hours.

The disclosed ORF56 and ORF49 polypeptides or a composition that includes an ORF56 or ORF49 polypeptide can be used to, e.g., enzymatically degrade a bacterial cell wall.

In another aspect the invention provides a method of treating a bacterial infection in a subject by administering an ORF56 or ORF49 polypeptide or a composition that includes an ORF56 or ORF49 polypeptide to the subject. The subject can be, e.g., a mammal, a primate, a human, a farm animal, a companion animal, a human, a poultry species, a cow, a horse, a goat, a cat, a sheep, a rodent, a dog, a pig, a chicken, a duck, a quail, or a goose. Show animals, e.g., elephants, lions, tigers, zebras, whales, dolphins, and bears can also be treated using the compositions of the present invention.

In various embodiments, the subject is a cow and the bacterial infection is bovine mastitis; the subject is a human and the bacterial infection is caused by a methicillin-resistant *Staphylococcus* species; or the subject is a poultry species and the bacterial infection is on the skin or feathers.

In another aspect the invention provides a method detecting a bacterium or identifying a disease causing bacterium by contacting the bacterium with an ORF56 or ORF49 polypeptide and detecting binding of the ORF56 or ORF49 polypeptide to the bacterium. In a preferred embodiment the ORF56 or ORF49 polypeptide is detectably labeled.

In one aspect the invention provides a method of disinfecting a surface, by contacting the surface with an ORF56 or ORF49 polypeptide or a composition that includes an ORF56 or ORF49 polypeptide. The disinfection method can be used to reduce or eliminate all bacteria on the surface or a plurality or a particular bacterial species or strain, e.g., a *Staphylococcus* species.

In one aspect the invention provides a substantially pure or isolated polypeptide characterized by at least one of the following properties: comprising at least about 85% identity over a segment of at least 17 amino acids to residues 1-808, 297-808, 363-808, 603-808, 620-808, or 691-805 of ORF56; comprising at least about 90% identity over a segment of at least 24 amino acids to residues 691-805 of ORF56; or comprising a plurality of distinct segments of a least 85% identity to ORF56, which segments do not overlap. Some additional properties include, e.g., distinct additional segments of at least about 75% identity over at least 17 amino acids to residues 691-805 of ORF56; distinct additional segments of at least 17 amino acids exhibiting at least about 65% identity over ORF56; at least 30% cell wall degrading activity of full length or native ORF56; a muralytic activity on a *Staphylococcus* bacterial strain at least about 50% of ORF56; another functional polypeptide sequence or domain, e.g., a signal sequence; or a detectable label; comprises at least residues 690 to 769 of ORF56; is a full length ORF56; corresponds to 1-808, 297-808, 363-808, Met-603-808, or 620-808 of ORF56; comprises a CHAP domain; is substantially free of other phage proteins; is substantially free of other proteinaceous materials; is combined with another antimicrobial agent, including an antibiotic; is admixed with a pharmaceutical excipient; is in a buffered or sterile composition; exhibits a bacterial cell wall degrading activity selected from muralytic, glucosamidase, amidase, or endopeptidase activity; exhibits bactericidal activity on multiple Gram-positive bacteria strains; exhibits bactericidal activity on a *Staphylococcus* bacteria strain; or exhibits bactericidal activity on one or more strains described as *S. aureus, S. epidermidis, S. lentis, S. simulans*, and *S. carnosus*.

In one aspect the invention provides an expression vector that expresses an isolated or recombinant nucleic acid that encodes an ORF56 or ORF49 polypeptide or a truncation of an ORF56 polypeptide disclosed herein. The invention also includes host cells that contain the ORF56 expression vector. A host cell can be, e.g., a eukaryote or prokaryote cell that is used to produce an ORF56 polypeptide or nucleic acid.

In one aspect the invention provides a substantially pure or isolated ORF56 polypeptide that has an antigen binding site of an antibody that binds selectively to a cell wall component. This ORF56 polypeptide can be, e.g., attached to a detectable label or provided as part of a kit with instructions that is used to evaluate the presence of target bacteria.

In one aspect the invention provides a method of enzymatically degrading the cell wall of a target bacterium, by exposing said cell wall to an ORF56 or ORF49 polypeptide. This method step can, e.g., be incorporated into a diagnostic to determine bacterial sensitivity; resulting in at least about a 5-fold decrease in sensitive bacterial population on a work or furniture surface; introduce the ORF56 or ORF49 polypeptide into an animal and results in at least a 5-fold decrease in sensitive bacterial population in a selected location in or on said animal; administer said polypeptide to an animal surface or compartment; be a means to generate dead or replication incompetent bacteria that can be inoculated into an individual; or be used to treat a skin, mucosal, urinary tract, respiratory tract, nasal cavity, gastrointestinal tract, or other bacterial infection. In other embodiments the decrease in a sensitive bacterial population is, e.g., a 2-fold, 3-fold, 4-fold, 7-fold, 9-fold, 10-fold, 20-fold, 25-fold, 50-fold, or 100-fold decrease, or even more.

In one aspect the invention provides a recombinant truncated ORF56 protein of SEQ ID NO: 1, wherein from 1 to 620 amino acids are truncated from the amino terminus of the ORF56 protein or wherein from 1 to 3 amino acids are truncated from the carboxy terminus of the ORF56 protein, and wherein the ORF56 protein has bacterial cell wall degrading activity. The remaining ORF56 protein can have about 80%, 90%, or 95% identity to the corresponding amino acid sequence in SEQ ID NO: 1.

The present invention provides a substantially pure or recombinant polypeptide exhibiting Staphylococcus strain murein degrading biological activity, the polypeptide comprising a tail associated murein-degrading enzyme (TAME) segment of a S. aureus infecting phage; and a heterologous S. aureus cell wall binding domain.

In certain preferred embodiments, the polypeptide has a protein backbone molecular weight of less than about 400 kDa, about 250 kDa; or about 100 kDa; or the polypeptide exhibits a peptidase, amidase, or hydrolase activity on a S. aureus murein; or the polypeptide is from the tail of a Caudovirales phage, e.g., a myoviridae, podoviridae, or siphoviridae phage. In other embodiments, the murein-degrading enzyme segment is from phage K ORF56, phage phi11 ORF49, or a phage derived from an MRSA. In various other embodiments, the cell wall binding domain is from a Staphylococcus bacterial protein, e.g., a Staph lysostaphin or a phage tail protein; or comprises: a bacterial SH3 segment; sequence from ORF56, S. simulans lysostaphin, or Phage L54a amidase; or any cell wall binding domain construct that increases murein-degrading activity of the polypeptide at least by 30 fold, as compared to a comparable polypeptide lacking function of the binding domain.

In one embodiment, the polypeptide comprises SEQ ID NO: 4.

Pharmaceutical compositions are also provided, e.g., where the polypeptide is in a cream or gel, or is in a single dose container, e.g., containing at least 10 nanogram of polypeptide. Such compositions may be in a controlled release formulation; applied to an implant, catheter, or medical device; or be in a sterile or buffered formulation.

In other preferred embodiments, the composition works on a Staphylococcus strain that is found in a nasal compartment; or that causes mastitis or infects burn or puncture wounds; or that is methicillin resistant or that is Vancomycin resistant. In another preferred embodiment, dressings, gauzes or the like used to cover wounds are impregnated with a TAME polypeptide or a chimeric protein comprising a TAME polypeptide to minimize the likelihood of bacterial infection. In a further embodiment, the wound is a puncture wound or a burn. In yet another embodiment, the individual with the wound has compromised immune system, e.g., resulting from HIV infection, organ transplantation and related treatments, stem cell or bone marrow transplantation, or chemotherapy. The TAME polypeptides and chimeric proteins comprising a TAME polypeptide can also be used to treat organs or blood products before transplantation into a recipient.

The invention further provides methods of treating a bacterial culture, the method comprising contacting said culture with a described chimeric polypeptide. Typically, the contacting decreases rate of growth of said culture by at least about 5 fold; or another antimicrobial therapy is also used; or the method uses a cocktail of polypeptides which target different strains of bacteria. Preferably, the treating decreases rate of growth of sensitive target bacteria by at least about 30%; the polypeptide is administered at a stoichiometry of at least about ten polypeptides for each target bacterium, or at least about 500 ng/ml; or the contacting of administering is continued for less than about 7 days. Alternatively, the culture comprises a Staphylococcal strain, a Gram-positive bacterium, or is an infection, or the culture may comprise mammalian cells or tissue.

The invention further provides a nucleic acid encoding the polypeptides, though the polypeptides may be generated by synthetic protein methods. And a cell comprising the nucleic acid is provided.

The invention further provides equivalent or related polypeptides derived from fusions of the TAME polypeptide sequence, or a segment of the TAME sequence containing a muralytic domain, to a segment of another polypeptide constituting a cell wall binding domain (CBD). These chimeric constructs will be designated as TAME-CBDs. The e.g., a substantially pure or recombinant polypeptide exhibiting Gram-positive strain murein-degrading biological activity, where the polypeptide comprises a modified, e.g., mutagenized, sequence of a Tail Associated Murein-degrading Enzyme (TAME) segment of a Gram-positive infecting phage; and/or a modified, e.g., mutagenized, heterologous Gram-positive cell wall binding domain. In these cases, "mutagenized" is primarily a form of the TAME in which regions of the complete TAME protein have been deleted, with the effect of increasing bactericidal or enzymatic activity, protein solubility, and/or protein stability, compared to the full-length TAME.

BRIEF DESCRIPTION OF THE DRAWINGS

FIG. 1 provides a table of TAME conserved domains identified in phages that infect Staphylococcus bacteria. Muralytic domains (MD) were identified and are referred to as TAME CD in the able.

DETAILED DESCRIPTION OF THE INVENTION

I. Introduction

The present study identified a heretofore unidentified entity, the phage K ORF56, which has now been shown to exhibit bactericidal activity. It is a component of certain myoviridae phage as a structural component of the virion with muralytic activity. The catalytic site was localized in the C-terminal part of the protein, and exhibits a Cysteine-Histidine dependent Aminohydrolase/Peptidase (CHAP) domain. See, e.g., Rigden, et al. (2003) Trends Biochem. Sci. 28:230-234. While the CHAP domain is found at the N-terminal regions of various genes, in a few genes the CHAP domain is found at the C-proximal segments of coding regions. Part of the invention is the understanding of a relationship between characterization of "cell wall degrading activity" assigned to phage proteins and capability to convert the degrading activity from a "lytic" function, which is evaluated under artificial conditions, into a bactericidal function under non-artificial conditions of typical bacterial growth circumstances. These "degrading activities" are likely to be new sources of unrecognized bactericidal activities for use under therapeutic conditions, and may include muraminidase, glucosaminidase, amidase, or endopeptidase activities. This activity can be identified, isolated, and has been shown, in various exemplary purified soluble protein constructs, to have bactericidal activity on target bacteria, outside of the context of the phage structures tested under highly artificial assay conditions. Moreover, recombinant constructs comprising such activities have significant advantageous properties as antimicrobial compositions and formulations.

Similarly, the siphoviridae phage phi11 has a murein-degrading activity (TAME), recognized in part by its pattern of gene structure.

This present study shows that the "hypothesized ORF56" of the *Staphylococcus* phage K has muralytic activity, and moreover that the recombinant protein product seems to be processed to a 23 10 protein from a 91 kD encoded "putative" translation product. Exposure of various strains of *Staphylococcus* bacteria to the 23 kD product indicates bactericidal activity. Truncation constructs indicate that the bactericidal activity is encoded in the C-proximal region of the protein translation product.

The present studies indicate that a 23 kD protein product which is generated from the ORF56 possesses a CHAP domain. Further, a 1610 truncated form of the 23 kD protein product encompassing the C-proximal region and the CHAP domain is also bactericidal. Based upon sequence homology searches, various other similar structures have been identified which are potential alternative sources for bactericidal activities. While there may be different muralytic activities, the scope of bacterial sensitivities are generally unstudied. Thus, various of these new activities may have relatively broad target anti-bacterial activities. Moreover, the small sizes of the polypeptides exhibiting these activities make them efficient for production and accessibility within a body or to relevant cell wall target components, e.g., peptidoglycans.

Phage therapy has recently received renewed attention as an alternative for prevention and/or treatment of bacterial infections. See Merril, et al. (2003) *Nat. Rev. Drug Discov.* 2:489-497; and Sulakvelidze, et al. (2001) *Antimicrob. Agents Chemother.* 45:649-659. Alternatively, phage-encoded endolysins have been proposed as effective agents for the control of infectious diseases caused by Gram-positive bacteria (Fischetti (2003) *Ann. N.Y. Acad. Sci.* 987:207-214). A recent paper on phage endolysins showed non-specificity of *Enterococcus* phage endolysins which act on *Streptococcus* and *Staphylococcus* other than *Enterococcus* (Yoong et al (2004) *J. Bact.* 186:4808-4812).

These muralytic or cell wall degrading labels assigned to phage components are found in many phage types, including the myoviridae, podoviridae, and siphoviridae classes.

Applicants worked with these TAME cell wall degrading activities testing for bactericidal activity under the artificial conditions applied to the term "lysis" entities, and found that their specific activities were relatively low. It became apparent that this limitation was intrinsic to the TAME activity, which has a biological role in generating an extremely limited degradation of the cell wall, sufficient to allow injection of the phage DNA but not to cause a deleterious effect on cell integrity. In particular, the rate of degradation of the cell wall leading to an effect on the bacterial growth was not striking, and in most situations was found to be insufficient for commercial therapeutic use.

Phage proteins have likely evolved to withstand the harsh environment outside of cells, and often outside of the body of an animal, and have evolved for inefficient killing of the target host cell. In fact, the life cycle of the phage requires that the cell NOT be killed in the infection process, else the phage life cycle would be aborted before replication. Thus, TAME proteins are inherently inefficient as bactericidal elements.

As such, Applicants further recognized that while the phage tail enzymes have the evolutionary purpose to assist the infection process, they have been evolved to NOT be efficient to the extent of killing the target host. Thus, if TAME proteins were to be useful as efficient bactericidal agents, the TAME proteins would require modification to do so. The present invention provides mutagenesis and screening methods that can be applied to identify cell wall degrading motifs that can direct TAME catalytic domains to a particular bacterium or a particular site on a bacterium. Using ORF56 as a model, Applicants were the first to recognize that phage TAME proteins can be converted from a marginal bactericidal agent into a highly efficient and robust bactericidal agent by, e.g., removing sequences which seem to prevent the full-length TAME polypeptide from exhibiting high bactericidal function, and/or fusing the remaining catalytic domain to a heterologous cell-wall binding domain. As noted above, these fusions, or chimeras, are here designated as TAME-CBDs.

Natural forms of these phage TAME proteins have limited bactericidal activities, as described. Applicants discovered that a targeting motif linked to the wall degrading domain affected a dramatic increase in the local concentration of the catalytic site at the cell wall substrate. Chimeric proteins form specific bacteria can be designed by, e.g. combining a catalytic segment from a TAME protein that acts on the appropriate cell wall structure as found naturally on the bacterial surface in its natural context and binding segment that has the appropriate affinity and targets the appropriate cell wall structure. Linking a targeting motif to a phage derived cell wall degrading segment can provide a number of fusion or bifunctional constructs to screen for desired bacteriostatic, bactericidal, or cell wall "lytic" activities.

Additional cell wall degrading enzymatic segments have been selected and constructs made to demonstrate the scope of the present invention. For example, segments derived from phage, typically tail structures, encoding enzymatic activities, e.g., cell wall degrading enzymes, have been used. Enzymatic activities have been isolated from various phage or bacterial sources, and shown to have similar activities. Similar activities are available from phage based structures, e.g., based upon sequence homology to known activities used by phage to gain access to the host, typically in an infection-related process. Others can be identified by gene organization of infection enzymes, e.g., in cassettes containing phage tail binding/wall penetration structures, in phage genomes (see the ORF49 of *S. aureus* phage phi11 cell wall hydrolase (NP_803302), which is a structural "counterpart" to the ORF56 in phage K. Other examples include ORF004 from *S. aureus* phage 69 (gi:66395297, YP_239591.1), cell wall hydrolase from phage PhiNM4 (gi:104641981, ABF73289.1), cell wall hydrolase from phi ETA2 (gi:122891778, YP_001004324.1), ORF004 from *S. aureus* phage 85 (gi:66394874, YP_239746.1), and ORF004 from phage ROSA (gi:66395969, YP_240329.1). Both of these domains or motifs may also be derived from prophage or "remnant phage" genomes left in a bacterial genome from an inactivated or incomplete phage genome. Prophages and methods to identify them are disclosed at, e.g., Canchaya et al., *Microbial. Mole. Biol. Rev.* 67:238-276 (2003), which is herein incorporated by reference for all purposes. Other activities may be derived from pyocins (bacteriocins) or phage related structures which may be incapable of proliferating as normal phage, but are produced or sustained as byproducts of incomplete genomes. Thus, proteins or encoding sequences may be isolated from structures representing viable phage, or derived therefrom. Moreover, each of these structures may serve as a starting point for mutagenesis to optimize activities under conditions desired for use, e.g., as described.

II. Tail Associated Murein-Degrading Enzymes (TAMES)

Tail Associated Murein-degrading Enzymes (TAMES) are defined as muralytic enzymes found in the bacteriophage particles and include those which will digest the bacterial cell wall preferably of a Gram-positive bacterium, but may also apply to those which can digest material of a Gram-negative or other bacterium. The activity will typically be a peptidoglycan degrading enzyme, and may have one or more muraminidase, glucosaminidase, transglycosylase, lysozyme, amidase or endopeptidase enzymatic activities. The enzyme may be capable of degrading of the cell wall, and may have even be characterized as "lytic" to the cell, but such a lytic characterization is under highly artificial conditions, compared to the normal environment of the phage infection process. Preferably, the enzymes are derived from phage structures, tails or tail-equivalents in podophage, or interior head proteins of podophage, which provide means for the phage genomic material to enter a bacterial host from the external environment; because these proteins are most commonly found in tail structures, for the purposes of this application, the entire class is called the TAME proteins. An example of a TAME protein associated with a tail-equivalent in podophage is the gp16 protein of Phage T7. The gp16 protein is a transglycosylase that attacks peptidoglycan. The gp16 protein aids in DNA injection, but is contained inside the capsid and when ejected during infection, seems to form part of tail. See, e.g., Molineux (1999) The T7 family of bacteriophages. In Encyclopedia of Molecular Biology. Creighton T E, ed. NY, John Wiley & Col, pp. 2495-2507.

The target bacteria will typically be those which affect or infect animals, particularly primates. However, various bacteriostatic or bactericidal applications would be advantageously pursued, as will certain public health problems. The bacteria will often fall into the Gram-positive class, though there are other pathological bacteria which are not clearly categorized into one or the other, including mycobacteria, spores, or other prokaryotes. Pathogenic or pathological bacterial targets are of most interest, both Gram-positive strains, e.g., *Staphylococcus* species, including aureus, and *Streptococcus* species, as well as Gram-negative. Particularly important Gram-negative target species include the genera *Escherichia*, particularly *coli*; *Pseudomonas*, particularly *aeruginosa*; *Campylobacter*; *Salmonella*; *Neisseria*; *Helicobacter*; and *Vibrio*. See, e.g., the Merck Manual and the Merck Veterinary Manual.

The ORF56 polypeptides disclosed herein can be used in combination with at least one other muralytic enzyme to, e.g., treat infection by one or more bacterial strains. Exemplary additional muralytic enzymes include, e.g., a phage p68 protein 16 and a Pal-type "lytic" enzyme. A phage p68 protein 16 is disclosed at, e.g., (Vybiral D et al. (2003), FEMs Microbiol Lett., 219, 275-283). Pal-type "lytic" enzymes are disclosed at, e.g., Fischetti, et al. (2005) US Pat App 20050208038.

As disclosed herein, TAME proteins can be identified by those of skill through a combination of sequence analysis and determination of the position of the encoding nucleic acid on a phage genome.

III. Definitions

A "cell wall degrading activity" is an enzymatic activity that degrades, breaks down, disintegrates, or diminishes or reduces the integrity of a bacterial cell. The term "lytic" is typically used to mean "cell wall degrading", partly because most (with certain exceptions) of the wall degrading catalytic activities are hydrolytic. Thus, much of the terminology used refers to "lytic" even if the catalytic mechanism does not involve hydrolysis. Alternatively degradation of certain defined or artificial substrates may be useful assays for "lytic" or static activity (on a populational basis for the target). "Cell wall lytic activity" in a phage context is usually a characterization assigned to a structure based upon testing under artificial conditions, but such characterization can be specific for bacterial species, families, genera, or subclasses (which may be defined by sensitivity). Therefore, a "bacterium susceptible to a cell wall degrading activity" describes a bacterium whose cell wall is degraded, broken down, disintegrated, or that has its cell wall integrity diminished or reduced by a particular cell wall degrading activity or activities. Many other "lytic activities" originate from the host bacterial cells, and are important in cell division or phage release. Other phage derived cell wall degrading activities are found on the phage and have evolved to serve in various penetration steps of phage infection but would be physiologically abortive to phage replication if they kill the host cell before phage DNA is injected into the cell. The structures useful in the penetration steps are particularly relevant to the present invention in that these activities operate on normal hosts from the exterior. In preferred embodiments, the cell wall degrading activity is provided by an enzyme that is a non-holin enzyme and/or that is a non-lysin enzyme. In other embodiments, the cell binding activity is provided by an enzyme that is a non-holin enzyme and/or that is a non-lysin enzyme.

A "cell binding domain" or "CBD" is typically a targeting motif, which recognizes the bacterial outer surface. In Gram-positive bacteria, the outer surface of the bacteria is typically the murein layer. Thus, the preferred binding segment for these targets will be cell surface entities, whether protein, lipid, sugar, or combination. Binding segments from known lysozymes, endolysins, and such are known and their properties easily found by PubMed or Entrez searches. Other proteins which bind to bacteria include the PGRPs described below, the TLRs, flagellum and pili binding entities, and phage tail proteins involved in target recognition. In a preferred embodiment, the CBD is fused to a TAME protein or to a cell wall degrading protein, both as disclosed herein. In a further preferred embodiment, the CBD is a heterologous domain as compared to the TAME protein or to cell wall degrading protein. That is, the CBD protein is derived from a non-TAME protein or a non-cell wall degrading protein, or is derived from a cell wall binding protein from a different phage, a bacterium or other organism. Thus, the heterologous CBD domain can be used to direct the TAME protein to specific target bacteria or can be used to increase the target range of the TAME protein.

An "environment" of a bacterium can include an in vitro or an in vivo environment. In vitro environments are typically found in a reaction vessel, in some embodiments using isolated or purified bacteria, but can include surface sterilization, general treatment of equipment or animal quarters, or public health facilities such as water, septic, or sewer facilities. Other in vitro conditions may simulate mixed specie populations, e.g., which include a number of symbiotically or interacting species in close proximity. Much of phage and bacterial study is performed in cultures in which the ratios of target host and phage are artificial and non-physiological. An in vivo environment preferably is in a host organism infected by the bacterium. In vivo environments include organs, such as bladder, kidney, lung, skin, heart and blood vessels, stomach, intestine, liver, brain or spinal chord, sensory organs, such as eyes, ears, nose, tongue, pancreas, spleen, thyroid, etc. In vivo environments include tissues, such as gums, nervous tissue, lymph tissue, glandular tissue, blood, sputum, etc., and may reflect cooperative interactions of different species whose survival may depend upon their interactions together. Catheter, implant, and monitoring or treatment devices which are introduced into the body may be sources of infection under normal usage. In vivo environments also include the surface of food, e.g., fish, meat, or plant materials. Meats include, e.g., beef, pork, chicken, turkey, quail, or other poultry. Plant materials include vegetable, fruits, or juices made from fruits and/or vegetables. In some embodiments surfaces that have come in contact with a bacterially-infected food product are treated with a TAME protein or a chimeric protein comprising a TAME protein, e.g., ORF56 or ORF49.

"Introducing" a composition to an environment includes administering a compound or composition, and contacting the bacterium with such. Introducing said compound or composition may often be effected by live bacteria which may produce or release such.

A "cell wall degrading protein" is a protein that has detectable, e.g., substantial, degrading activity on a cell wall or components thereof. "Lytic" activity may be an extreme form or result of the degrading activity. Exemplary bactericidal polypeptides include, e.g., ORF56 or ORF49 products, structurally related entities, mutant and variants thereof, and other related constructs derived therefrom or from the twort, K, G1, or phi11 phage. Particular preferred sequences are derived, e.g., from ORF005 from *Staph* phage G1 (see gi:66394954, YP_240921.1), from ORF007 from *Staph* phage Twort (see gi:66391262, YP_238566.1), or from *Listeria* phage P100 (see gi:82547634, YP_406405.1). Similar degrading activities will be identified by their location on the phage tails or target host contact points of natural phage, mutated phage remnants (e.g., pyocins or bacteriocins), or encoded by prophage sequences. Preferred segments are derived, e.g., from ORF56 or ORF49, *S. simulans* lysostaphin (lss), *S. aureus* LytM peptidase, *S. capitis* ALE1, and other phage tail muralytic polypeptides.

An "ORF56 polypeptide" or grammatical variant thereof, refers to a bacteriocidal or bacteriocidal activity encoded by the ORF56 of *Staphylococcus* phage K (associated structural features are related to gi|48696445). Exemplary variant ORF56 polypeptides include polypeptide polymorphic variants, alleles, mutants, and interspecies homologs that: (1) have an amino acid sequence that has greater than about 60% amino acid sequence identity, about 65%, 70%, 75%, 80%, 85%, 90%, preferably about 91%, 92%, 93%, 94%, 95%, 96%, 97%, 98% or 99% or greater amino acid sequence identity, preferably over one or more regions, e.g., of at least about 8, 12, 17, 25, 33, 50, 65, 80, 100, 200, or more amino acids, to an amino acid sequence encoded by an ORF56 nucleic acid from *Staphylococcus* phage K, see, e.g., Accession Number YP_024486, or to an amino acid sequence of a muralytic polypeptide from *Staph* phage Twort, K, or G1; (2) bind to antibodies, e.g., polyclonal antibodies, raised against a substantially purified immunogen comprising an amino acid sequence of an active fragment of ORF56, and conservatively modified variants thereof; (3) specifically hybridize under stringent hybridization conditions to an anti-sense strand corresponding to a natural nucleic acid sequence encoding the ORF56 polypeptide, and conservatively modified variants thereof; (4) have a nucleic acid sequence that has greater than about 65%, 70%, 75%, 80%, 85%, 90%, or 95%, preferably greater than about 96%, 97%, 98%, 99%, or higher nucleotide sequence identity, preferably over a region of at least about 25, 50, 100, 150, 200, 250, 300, 400, 500, 600, 700, etc., or more nucleotides, to the ORF56 encoding nucleic acid or a nucleic acid encoding fragment thereof. Particularly preferred segments are derived from the CHAP domain. The nucleic acids and proteins of the invention include both natural or recombinant molecules. The full length ORF56 polypeptide and N terminal truncated fragments thereof, as small as about 16 kD, typically have degradative activity on cell wall components. Assays for degrading activity on cell wall components can be performed according to methods known to those of skill in the art, and as described herein. In preferred embodiments, ORF56 polypeptide has bactericidal activity against various *Staphylococcus* strains of bacteria, including the *aureus*, *epidermidis*, *lentis*, and *carnosus* species. Analogous measures of comparison may be applicable to other sequences, e.g., ORF49, described herein.

Nucleic acids encoding cell wall degrading polypeptides can, in some embodiments, be amplified using PCR primers based on the sequence of described cell wall degrading polypeptides. For example, nucleic acids encoding ORF56 polypeptide variants and fragments thereof, as well as likely wall degrading activity candidates, can be amplified using primers. See, e.g., Vybiral, et al. (2003) *FEMS Microbiol. Lett.* 219:275-283. Thus, cell wall degrading polypeptides and fragments thereof include polypeptides that are encoded by nucleic acids that are amplified by PCR based on the sequence of the identified cell wall degrading polypeptides. In a preferred embodiment, a bactericidal or bacteriostatic polypeptide or fragment thereof is encoded by a nucleic acid that is amplified by primers relevant to the ORF56 or ORF49 sequences described.

A "phage particle component" refers to, e.g., a head or tail component of a phage, e.g., Phage K, Twort, G1, or phi11. However, the invention provides that many different phage types may be sources of the "lytic" activity loosely ascribed to the phage components. See, e.g., Piuri and Hatfull (2006) "A peptidoglycan hydrolase motif within the mycobacteriophage TM4 tape measure protein promotes efficient infection of stationary phase cells" *Molecular Microbiology* 62:1569-1585. A phage nucleic acid refers to a nucleic acid component of a phage and includes double and single stranded nucleic acids, e.g., DNA, RNA, or hybrid molecules. Related sequences may be found in prophages or incomplete phage genomes, typically found integrated into the bacterial host chromosome. Tail components typically mediate the recognition and attachment of the phage to the target host, and may possess cell wall degrading activities which assist in penetration of phage components into the host.

"GMP conditions" refers to good manufacturing practices, e.g., as defined by the Food and Drug Administration of the United States Government. Analogous practices and regulations exist in Europe, Japan, and most developed countries.

The term "substantially" in the above definitions of "substantially pure" generally means at least about 60%, at least about 70%, at least about 80%, or more preferably at least about 90%, and still more preferably at least about 95% pure, whether protein, nucleic acid, or other structural or other class of molecules.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutarnate, and O-phosphoserine. Amino acid analog refers to a compound that has the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain a basic chemical structure as a naturally occurring amino acid. Amino acid mimetic refers to a chemical compound that has a structure that is different from the general chemical structure of an amino acid, but that functions in a manner similar to a naturally occurring amino acid.

"Protein", "polypeptide", or "peptide" refers to a polymer in which most or all of the monomers are amino acids and are joined together through amide bonds, alternatively referred to as a polypeptide. When the amino acids are α-amino acids, either the L-optical isomer or the D-optical isomer can be used. Additionally, unnatural amino acids, e.g., β-alanine, phenylglycine, and homoarginine, are also included. Amino acids that are not gene-encoded may also be used in the present invention. Furthermore, amino acids that have been modified to include appropriate structure or reactive groups may also be used in the invention. The amino acids used in the present invention may be the D- or L-isomer, or mixtures thereof. The L-isomers are generally preferred. In addition, other peptidomimetics are also useful in the present invention. For a general review, see, Spatola, in Weinstein, et al. (eds. 1983) CHEMISTRY AND BIOCHEMISTRY OF AMINO ACIDS, PEPTIDES AND PROTEINS, Marcel Dekker, New York, p. 267.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. In particular, fusions of sequence may be generated, e.g., incorporating an upstream secretion cassette upstream of desired sequence to generate secreted protein product.

A "fusion protein" refers to a protein comprising amino acid sequences that are in addition to, in place of, less than, and/or different from the amino acid sequences encoding the original or native full-length protein or subsequences thereof. More than one additional domain can be added to a cell wall lytic protein as described herein, e.g., an epitope tag or purification tag, or multiple epitope tags or purification tags. Additional domains may be attached, e.g., which may add additional lytic activities (on the target or associated organisms of a mixed colony or biofilm), bacterial capsule degrading activities, targeting functions, or which affect physiological processes, e.g., vascular permeability. Alternatively, domains may be associated to result in physical affinity between different polypeptides to generate multichain polymer complexes.

The term "nucleic acid" refers to a deoxyribonucleotide, ribonucleotide, or mixed polymer in single- or double-stranded form, and, unless otherwise limited, encompasses known analogues of natural nucleotides that hybridize to nucleic acids in a manner similar to naturally occurring nucleotides. Unless otherwise indicated or by context, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes typically include at least promoters and/or transcription termination signals. Typically, the recombinant expression cassette includes a nucleic acid to be transcribed (e.g., a nucleic acid encoding a desired polypeptide), and a promoter. Additional factors necessary or helpful in effecting expression may also be used, e.g., as described herein. In certain embodiments, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In certain embodiments, a recombinant expression cassette encoding an amino acid sequence comprising a lytic activity on a cell wall is expressed in a bacterial host cell.

A "heterologous sequence" or a "heterologous nucleic acid", as used herein, is one that originates from a source foreign to the particular host cell, or, if from the same source, is modified from its original form. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and, e.g., HPLC or a similar means for purification may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the sequence comparison algorithms or by visual inspection.

The phrase "substantially identical," in the context of two nucleic acids or proteins, refers to two or more sequences or subsequences that have, over the appropriate segment, at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that corresponds to at least about 13, 15, 17, 23, 27, 31, 35, 40, 50, or more amino acid residues in length, more preferably over a region of at least about 100 residues, and most preferably the sequences are substantially identical over at least about 150 residues. Longer corresponding nucleic acid lengths are intended, though codon redundancy may be considered. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these and related algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, Ausubel, et al., eds., Current Protocols, a joint venture between Greene Publishing Associates, Inc. and John Wiley & Sons, Inc. (1995 and Supplements) (Ausubel)).

Examples of algorithms that are suitable for determining percent sequence identity and sequence similarity are the BLAST and BLAST 2.0 algorithms, which are described in Altschul, et al. (1990) *J. Mol. Biol.* 215:403-410 and Altschuel, et al. (1977) *Nucleic Acids Res.* 25:3389-3402, respectively. Software for performing BLAST analyses is publicly available through the National Center for Biotechnology Information (ncbi.nlm.nih.gov/) or similar sources. This algorithm involves first identifying high scoring sequence pairs (HSPs) by identifying short "words" of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Nat'l Acad. Sci. USA* 89:10915).

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at each position where an arginine is specified by a codon, the codon can be altered to another of the corresponding codons described without altering the encoded protein. Such nucleic acid variations are "silent variations," which are one species of "conservatively modified variations." Each polynucleotide sequence described herein which encodes a protein also describes possible silent variations, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is typically implicit in each described sequence.

Those of skill recognize that many amino acids can be substituted for one another in a protein without affecting the function of the protein, e.g., a conservative substitution can be the basis of a conservatively modified variant of a protein such as the disclosed cell wall lytic proteins. An incomplete list of conservative amino acid substitutions follows. The following eight groups each contain amino acids that are normally conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton (1984) *Proteins*).

Furthermore, one of skill will recognize that individual substitutions, deletions, or additions which alter, add, or delete a single amino acid or a small percentage of amino acids (typically less than 5%, more typically less than 1%) in an encoded sequence are effectively "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., cell wall lytic proteins, and nucleic acids which encode proteins yield essentially identical products. For example, due to the degeneracy of the genetic code, "silent substitutions" (e.g., substitutions of a nucleic acid sequence which do not result in an alteration in an encoded protein) are an implied feature of each nucleic acid sequence which encodes an amino acid. As described herein, sequences are preferably optimized for expression in a particular host cell used to produce the cell wall lytic proteins (e.g., yeast, human, and the like). Similarly, "conservative amino acid substitutions," in one or a few amino acids in an amino acid sequence are substituted with different amino acids with highly similar properties, are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence generally are also "conservatively modified variations".

The practice of this invention can involve the construction of recombinant nucleic acids and the expression of genes in host cells, preferably bacterial host cells. Optimized codon usage for a specific host will often be applicable. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, Ausubel, et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect, mammalian, and fungal cells (e.g., *Aspergillus niger*).

Examples of protocols sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis, et al. (1987) U.S. Pat. No. 4,683,202; *PCR Protocols A Guide to. Methods and Applications* (Innis, et al. eds) Academic Press Inc. San Diego, Calif. (1990) (Innis); Amheim and Levinson (Oct. 1, 1990) *C&EN* 36-47; *The Journal Of NIH Research* (1991) 3:81-94; (Kwoh, et al. (1989) *Proc. Nat'l Acad. Sci. USA* 86:1173; Guatelli, et al. (1990) *Proc. Nat'l Acad. Sci. USA* 87:1874; Lomeli, et al. (1989) *J. Clin. Chem.* 35:1826; Landegren, et al. (1988) *Science* 241:1077-1080; Van Brunt (1990) *Biotechnology* 8:291-294; Wu and Wallace (1989) *Gene* 4:560; and Barringer, et al. (1990) *Gene* 89:117. Improved methods of cloning in vitro amplified nucleic acids are described in Wallace, et al., U.S. Pat. No. 5,426,039.

IV. Commercial Applications

Various applications of the described enzymatic activities can be immediately recognized. One important application is as antibacterial treatment of articles which may be contaminated in normal use. Locations, equipment, environments, or the like where target bacteria may be public health hazards may be treated using such entities. Locations of interest include public health facilities where the purpose or opportunity exists to deal with target bacteria containing materials. These materials may include waste products, e.g., liquid, solid, or air. Aqueous waste treatment plants may incorporate such to eliminate the target from effluent, whether by treatment with the enzyme entities directly, or by release of cells which produce such. Solid waste sites may introduce such to minimize possibility of target host outbreaks. Conversely, food preparation areas or equipment need to be regularly cleaned, and the invention provides compositions and means to effectively eliminate target bacteria. Medical and other public environments subject to contamination may warrant similar means to minimize growth and spread of target microorganisms. The methods may be used in contexts where sterilization elimination of target bacteria is desired, including air filtration systems for an intensive care unit.

Alternative applications include use in a veterinary or medical context. Means to determine the presence of particular bacteria, or to identify specific targets may utilize the effect of selective agents on the population or culture. Inclusion of bacteristatic or bactericidal activities to cleaning agents, including washing of animals and pets, may be desired.

The ORF56 and related polypeptides can be used to treat bacterial infections of, e.g., humans or animals. These polypeptides can be administered prophylactically or can be administered to a subject that has contracted a bacterial infection. In a preferred embodiment, ORF56 polypeptides are used to treat infections caused by bacteria that replicate slowly as the killing mechanism does not depend upon host cell replication. Many antibacterial agents, e.g., antibiotics, are most useful against replicating bacteria. Bacteria that replicate slowly have doubling times of, e.g., about 1-72 hours, 1-48 hours, 1-24 hours, 1-12 hours, 1-6 hours, 1-3 hours, or 1-2 hours.

In a preferred embodiment, these proteins are used to treat humans or other animals that are infected with a *Staphylococcus* species. In another preferred embodiment, the ORF56 or ORF49 proteins are used to treat humans or other animals that are infected with a methicillin-resistant *Staphylococcus* species.

V. Administration

The route of administration and dosage will vary with the infecting bacteria strain(s), the site and extent of infection (e.g., local or systemic), and the subject being treated. The routes of administration include but are not limited to: oral, aerosol or other device for delivery to the lungs, nasal spray, intravenous (IV), intramuscular, intraperitoneal, intrathecal, intraocular, vaginal, rectal, topical, lumbar puncture, intrathecal, and direct application to the brain and/or meninges. Excipients which can be used as a vehicle for the delivery of the therapeutic will be apparent to those skilled in the art. For example, the enzyme could be in lyophilized form and be dissolved just prior to administration by IV injection. The dosage of administration is contemplated to be in the range of about 0.03, 0.1, 0.3, 1, 3, 10, 30, 100, 300, 1000, 3000, 10000 or more enzyme molecules per bacterium in the host infection. Depending upon the size of the protein, which may itself be tandemly associated, or in multiple subunit form (dimer, trimer, tetramer, pentamer, and the like) or in combination with one or more other entities, e.g., enzymes or fragments of different specificity, the dose may be about 1 million to about 10 trillion/per kg/per day, and preferably about 1 trillion/per kg/per day, and may be from about 10E6 killing units/kg/day to about 10E13 killing units/kg/day.

Methods to evaluate killing capacity may be similar to methods used by those of skill to evaluate intact replicating phage, e.g., plaque forming units or pfu, though killing units may be better evaluated by determining the number of surviving bacteria after titration of the killing units. Killing quantification is more distinct, however, since non-replicating phage will not form plaques on bacterial lawns. Thus, serial dilution methods to evaluate the quantity of "killing" units are conveniently used in place of standard pfu. Serial dilutions of bacterial cultures exposed to the killing compositions can quantify killing units. Alternatively, comparing total bacterial counts with viable colony units can establish what fraction of bacteria is actually viable, and by implication, what fraction have been susceptible to the killing constructs. Other measures of activity on artificial or specially prepared substrates can often be used as surrogate measures of killing units.

The therapeutic(s) are typically administered until successful elimination of the pathogenic bacteria is achieved, though broad spectrum formulations may be used while specific diagnosis of the infecting strain is being determined. Thus the invention contemplates single dosage forms, as well as multiple dosage forms of the compositions of the invention, as well as methods for accomplishing sustained release means for delivery of such single and multi-dosages forms.

With respect to the aerosol administration to the lungs or other mucosal surfaces, the therapeutic composition is incorporated into an aerosol formulation specifically designed for administration. Many such aerosols are known in the art, and the present invention is not limited to any particular formulation. An example of such an aerosol is the Proventil inhaler manufactured by Schering-Plough, the propellant of which contains trichloromonofluoromethane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. The number of enzyme killing units to be administered per aerosol treatment will typically be in the range of about 10E6 to 10E13 killing units, and preferably about 10E12 killing units.

Methods to evaluate killing capacity are often similar to many methods used in working with intact replicating phage. In particular, killing quantification is more difficult since the non-replicating phage will not form plaques on bacteria. Thus, serial dilution methods to evaluate the quantity of "killing" units will be performed similarly to standard pfu (plaque forming units), but cannot make use of the killing and amplification which occurs on a bacterial lawn. Serial dilutions of bacterial cultures exposed to the killing compositions can quantify killing units. Alternatively, comparing total bacterial counts with viable colony units can establish what fraction of bacteria are actually viable, and by implication, what fraction have been susceptible to the killing constructs. Other means for evaluating stasis activity may include release of intracellular contents, whether natural or loaded, or enzymatic activity on defined or prepared substrates which correspond to natural cell wall structures.

Typically, the killing will decrease bacterial replication capacity by at least about 3 fold, and may affect it by about 10, 30, 100, 300, etc., to many orders of magnitude. However, even slowing the rate of bacterial replication without killing may have significant therapeutic or commercial value. Preferred genetic inactivation efficiencies may be 0.1, 0.2, 0.3, 0.5, 0.8, 1, 1.5, 2.0, 2.5, 3.0, 3.5, 4, 5, 6, 7, 8, or more log units.

VI. Formulations

The invention further contemplates pharmaceutical compositions comprising at least one wall degrading enzyme, e.g., muramidase, of the invention provided in a pharmaceutically acceptable excipient. The formulations and pharmaceutical compositions of the invention thus contemplate formulations comprising an isolated enzyme segment specific for a bacterium; a mixture of two, three, five, ten, or twenty or more enzymes that affect the same or typical bacterial host; and a mixture of two, three, five, ten, or twenty or more enzymes that affect different bacteria or different strains of the same bacterium, e.g., a cocktail mixture of enzymes that collectively inhibit the growth of multiple strains of *Staphylococcus aureus*. In this manner, the compositions of the invention can be tailored to the needs of the patient. The compounds or compositions will typically be sterile or near sterile.

By "therapeutically effective dose" herein is meant a dose that produces effects, bacteriostatic or preferably bactericidal, for which it is administered. The exact dose will depend on the purpose of the treatment, and will be ascertainable by one skilled in the art using known techniques. See, e.g., Ansel, et al. *Pharmaceutical Dosage Forms and Drug Delivery*; Lieberman (1992) *Pharmaceutical Dosage Forms* (vols. 1-3), Dekker, ISBN 0824770846, 082476918X, 0824712692, 0824716981; Lloyd (1999) *The Art, Science and Technology of Pharmaceutical Compounding*; and Pickar (1999) *Dosage Calculations*. As is known in the art, adjustments for protein degradation, systemic versus localized delivery, and rate of new protease synthesis, as well as the age, body weight, general health, sex, diet, time of administration, drug interaction, spectrum of bacterial components in the colony, and the severity of the condition may be necessary, and will be ascertainable with some experimentation by those skilled in the art.

Various pharmaceutically acceptable excipients are well known in the art. As used herein, "pharmaceutically acceptable excipient" includes a material which, when combined with an active ingredient of a composition, allows the ingredient to retain biological activity and without causing disruptive reactions with the subject's immune system. Such may include stabilizers, preservatives, salt, or sugar complexes or crystals, and the like.

Exemplary pharmaceutically carriers include sterile aqueous of non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms.

A composition comprising an enzyme of the invention may also be lyophilized using means well known in the art, e.g., for subsequent reconstitution and use according to the invention.

Also of interest are formulations for liposomal delivery, and formulations comprising microencapsulated enzymes, including sugar crystals. Compositions comprising such excipients are formulated by well known conventional methods (see, e.g., *Remington's Pharmaceutical Sciences*, Chapter 43, 14th Ed., Mack Publishing Col, Easton Pa. 18042, USA).

In general, pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

The pharmaceutical composition can comprise other components in addition to the "lytic" enzyme. In addition, the pharmaceutical compositions may comprise more than one active ingredient, e.g., two or more, three or more, five or more, or ten or more different enzymes, where the different enzymes may be specific for the same, different, or accompanying bacteria. For example, the pharmaceutical composition can contain multiple (e.g., at least two or more) defined wall degrading enzymes, wherein at least two of the enzymes in the composition have different bacterial specificity. In this manner, the therapeutic composition can be adapted for treating a mixed infection of different bacteria, or may be a composition selected to be effective against various types of infections found commonly in a particular institutional environment. A select combination may result, e.g., by selecting different groups of wall degrading or "lytic" entities derived from various bacteriophage of differing specificity so as to contain at least one component effective against different or critical bacteria (e.g., strain, species, etc.) suspected of being present in the infection (e.g., in the infected site). As noted above, the wall degrading enzyme can be administered in conjunction with other agents, such as a conventional antimicrobial agent. In some embodiments, it may be desirable to administer the enzyme and antibiotic within the same formulation.

VII. Methodology

Some aspects of practicing the present invention involve well-known methods general clinical microbiology, general methods for handling bacteriophage, and general fundamentals of biotechnology, principles and methods. References for such methods are listed below and are herein incorporated by reference for all purposes.

A. General Clinical Microbiology

General microbiology is the study of the microorganisms. See, e.g., Sonenshein, et al. (eds. 2002) *Bacillus Subtilis and Its Closest Relatives: From Genes to Cells* Amer. Soc. Microbiol., ISBN: 1555812058; Alexander and Strete (2001) *Microbiology: A Photographic Atlas for the Laboratory* Benjamin/Cummings, ISBN: 0805327320; Cann (2001) *Principles of Molecular Virology* (Book with CD-ROM; 3d ed.), ISBN: 0121585336; Garrity (ed. 2005) *Bergey's Manual of Systematic Bacteriology* (2 vol. 2d ed.) Plenum, ISBN:

0387950400; Salyers and Whitt (2001) *Bacterial Pathogenesis: A Molecular Approach* (2d ed.) Amer. Soc. Microbiol., ISBN: 155581171X; Tiemo (2001) *The Secret Life of Germs: Observations and Lessons from a Microbe Hunter* Pocket Star, ISBN: 0743421876; Block (ed. 2000) *Disinfection, Sterilization, and Preservation* (5th ed.) Lippincott Williams & Wilkins Publ., ISBN: 0683307401; Cullimore (2000) *Practical Atlas for Bacterial Identification* Lewis Pub., ISBN: 1566703921; Madigan, et al. (2000) *Brock Biology of Microorganisms* (9th ed.) Prentice Hall, ASIN: 0130819220; Maier, et al. (eds. 2000) *Environmental Microbiology* Academic Pr., ISBN: 0124975704; Tortora, et al. (2000) *Microbiology: An Introduction* including Microbiology Place™ Website, Student Tutorial CD-ROM, and Bacteria ID CD-ROM (7th ed.), Benjamin/Cummings, ISBN 0805375546; Demain, et al. (eds. 1999) *Manual of Industrial Microbiology and Biotechnology* (2d ed.) Amer. Soc. Microbiol., ISBN: 1555811280; Flint, et al. (eds. 1999) *Principles of Virology: Molecular Biology, Pathogenesis, and Control* Amer. Soc. Microbiol., ISBN: 1555811272; Murray, et al. (ed. 1999) *Manual of Clinical Microbiology* (7th ed.) Amer. Soc. Microbiol., ISBN: 1555811264; Burlage, et al. (eds. 1998) *Techniques in Microbial Ecology* Oxford Univ. Pr., ISBN: 0195092236; Forbes, et al. (1998) *Bailey & Scott's Diagnostic Microbiology* (10th ed.) Mosby, ASIN: 0815125356; Schaechter, et al. (ed. 1998) *Mechanisms of Microbial Disease* (3d ed.) Lippincott, Williams & Wilkins, ISBN: 0683076051; Tomes (1998) *The Gospel of Germs: Men, Women, and the Microbe in American Life* Harvard Univ. Pr., ISBN: 0674357078; Snyder and Champness (1997) *Molecular Genetics of Bacteria* Amer. Soc. Microbiol., ISBN: 1555811027; Karlen (1996) *MAN AND MICROBES: Disease and Plagues in History and Modern Times* Touchstone Books, ISBN: 0684822709; and Bergey (ed. 1994) *Bergey's Manual of Determinative Bacteriology* (9th ed.) Lippincott; Williams & Wilkins, ISBN: 0683006037.

B. General Methods for Handling Bacteriophage

General methods for handling bacteriophage are well known, see, e.g., Snustad and Dean (2002) *Genetics Experiments with Bacterial Viruses* Freeman; O'Brien and Aitken (eds. 2002) *Antibody Phage Display: Methods and Protocols* Humana; Ring and Blair (eds. 2000) *Genetically Engineered Viruses* BIOS Sci. Pub.; Adolf (ed. 1995) *Methods in Molecular Genetics: Viral Gene Techniques* vol. 6, Elsevier; Adolf (ed. 1995) *Methods in Molecular Genetics: Viral Gene Techniques* vol. 7, Elsevier; and Hoban and Rott (eds. 1988) *Molec. Biol. of Bacterial Virus Systems* (Current Topics in Microbiology and Immunology No. 136) Springer-Verlag.

C. General Fundamentals of Biotechnology, Principles and Methods

General fundamentals of biotechnology, principles and methods are described, e.g., in Alberts, et al. (2002) *Molecular Biology of the Cell* (4th ed.) Garland ISBN: 0815332181; Lodish, et al. (1999) *Molecular Cell Biology* (4th ed.) Freeman, ISBN: 071673706X; Janeway, et al. (eds. 2001) *Immunobiology* (5th ed.) Garland, ISBN: 081533642X; Flint, et al. (eds. 1999) *Principles of Virology: Molecular Biology, Pathogenesis, and Control*, Am.

Soc. Microbiol., ISBN: 1555811272; Nelson, et at (2000) *Lehninger Principles of Biochemistry* (3d ed.) Worth, ISBN: 1572599316; Freshney (2000) *Culture of Animal Cells: A Manual of Basic Technique* (4th ed.) Wiley-Liss; ISBN: 0471348899; Arias and Stewart (2002) *Molecular Principles of Animal Development*, Oxford University Press, ISBN: 0198792840; Griffiths, et al. (2000) *An Introduction to Genetic Analysis* (7th ed.) Freeman, ISBN: 071673771X; Kierszenbaum (2001) *Histology and Cell Biology*, Mosby, ISBN: 0323016391; Weaver (2001) *Molecular Biology* (2d ed.) McGraw-Hill, ISBN: 0072345179; Barker (1998) *At the Bench: A Laboratory Navigator* CSH Laboratory, ISBN: 0879695234; Branden and Tooze (1999) *Introduction to Protein Structure* (2d ed.), Garland Publishing; ISBN: 0815323050; Sambrook and Russell (2001) *Molecular Cloning: A Laboratory Manual* (3 vol., 3d ed.), CSH Lab. Press, ISBN: 0879695773; and Scopes (1994) *Protein Purification: Principles and Practice* (3d ed.) Springer Verlag, ISBN: 0387940723.

D. Mutagenesis; Site Specific, Random, Shuffling

Based upon the structural and functional descriptions provide herein, homologs and variants may be isolated or generated which may optimize preferred features. Thus, additional catalytic segments of phage penetration functions may be found by structural homology, or by evaluating entities found in characteristic gene organization motifs. Phage tail genes are typically found in particular gene arrangements, and other entities found in the corresponding arrangements can be tested for a cell wall degrading function. These may also serve as the starting points to screen for variants of the structures, e.g., mutagenizing such structures and screening for those which have desired characteristics, e.g., broader substrate specificity. Standard methods of mutagenesis may be used, see, e.g., Johnson-Boaz, et al. (1994) *Mol. Microbiol.* 13:495-504; U.S. Pat. Nos. 6,506,602, 6,518,065, 6,521,453, 6,579,678, and references cited by or therein.

Binding segments may be similarly identified, and prevalent or specific target motifs may be screened for binding domains which interact specifically with them. Many of those targets may be highly expressed proteins, carbohydrate, or lipid containing structures found on the various potential target strains. While many proteins are known which bind to cell walls, two families include the peptidoglycan recognition proteins (PGRPs, see, e.g., Dziarski and Gupta (2006) "The peptidoglycan recognition proteins (PGRPs)" Genome Biol. 7:232, PMID: 16930467; Dziarski and Gupta (2006) "Mammalian PGRPs: novel antibacterial proteins" *Cell Microbiol.* 8:1059-69, PMID: 16819960; Lu, et al. (2006) "Peptidoglycan recognition proteins are a new class of human bactericidal proteins" *J. Biol. Chem.* 281:5895-5907; Dziarski (2004) "Peptidoglycan recognition proteins (PGRPs)" *Mol. Immunol.* 40:877-886, PMID: 14698226; Guan, et al. (2004) "Crystal structure of the C-terminal peptidoglycan-binding domain of human peptidoglycan recognition protein la" *J. Biol. Chem.* 279:31873-882; Liu, et al. (2001) "Peptidoglycan Recognition Proteins: a novel family of four human innate immunity pattern recognition molecules" *J. Biol. Chem.* 276:34686-694; and Werner, et al. (2000) "A family of peptidoglycan recognition proteins in the fruit fly *Drosophila melanogaster*" *Proc. Nat'l Acad. Sci. USA* 97:13772-777) found in species from insects to mammals. There is a conserved segment of about 160 amino acids found at the C-terminus of these proteins, and others may be found by PubMed or sequence searches. Another group of proteins which bind to bacteria is the toll-like receptors (TLR), particularly TLR4 which directly detects bacterial LPS; TLR2 which binds to bacterial lipoproteins, peptidoglycan, and yeast zymosan; TLR3 which binds double stranded RNA; and TLR5, which recognizes flagelin, the protein on bacterial flagella. Pili structures found on the outside of the bacterial cell may be another structure for which proteins target for binding. Mutagenesis may broaden binding selectivity or increase stability of segments or the entire construct, deletion strategies may eliminate extraneous segments.

The components of the Gram-positive bacteria cell wall may be shared with components of the Gram-negative cell wall, or possibly with other mycobacteria or spores. However, there may be additional layers of wall in the Gram-negative which may also serve as additional barriers to phage access. Other activities derived from phage or elsewhere may be combined to penetrate the more complex Gram-negative cell wall structures. In particular, multiple catalytic segments may provide multiple activities, which may function synergistically, within a single construct, or which can provide synergistic effect when combined with another therapeutic, e.g., antibiotic or antimicrobial.

A targeting moiety may increase a local concentration of a catalytic fragment, but a linker of appropriate length may also increase the number of wall degrading events locally. Thus, linkers compatible with the target and catalytic motifs or of appropriate length may be useful and increase the catalytic penetration activity leading to stasis or killing of target bacteria.

Part of the conceptual advance from the invention is recognition that phage have been selected to survive outside of cells, often under biologically inhospitable conditions. Thus, the structures are likely to be particularly hardy and robust, and resistant to the environmental conditions which might otherwise inactivate a phage. Bacteria which live in inhospitable environments, e.g., extreme environments of temperature, salt, oxidizing or reactive extremes, high pressure, and others, are likely to have phage which are particularly adapted to survive outside the cells. So these will be hardy, resistant to those extremes, and probably can survive them more readily than proteins which have not been subjected to similar selection. And polypeptides derived from those sources are likely to be more stable in various purification processes, storage, and pharmacological conditions of use. Yet another aspect of the invention come from a presumption that the purpose of TAME structures is to recognize and bind to the target bacterium, but not to kill the cell quickly. Thus, the TAME have evolved to not be very efficient at killing under conditions of commercially feasible use. The ORF56 constructs were tested to see whether the marginal commercially viable bactericidal activity could be increased. In fact, a combination of polypeptide deletion and the attachment of a binding function increased the activity to a more attractive level of commercial feasibility. The linkage to a cell wall targeting moiety can increase the local substrate concentration at the cell wall degrading active site, and the deletion of sequence from the natural TAME may delete some of the features which may have been adopted to limit the bactericidal rate to prevent killing of the host before the phage can replicate within the cell. And these features are found ubiquitously, as are phage, as starting points for collecting and screening for the desired properties for these uses.

E. Screening

Screening methods can be devised for evaluating mutants or new candidate functional segments. A purified preparation of the phage particles could be screened for presence of such gene products on the phage structure. Binding may use crude bacteria cultures, isolated bacterial cell wall components, peptidoglycan preparations, synthetic substrates, or purified reagents to determine the affinity and number of target bindings on target cells. Penetration or wall degrading assays may be devised to evaluate integrity of the cell walls of target strains, lawn inhibition assays, viability tests of cultures, activity on cell wall preparations or other substrates (e.g., as described for binding motifs), or release of components (e.g., sugars, amino acids, polymers) of the cell wall upon catalytic action. Amidase activity may be measured by release of soluble N-acetyl hexose amines (e.g., modified Morgan-Elson reaction) or endopeptidase activity by assay for free amino groups (L-alanine for ala-gly endopeptidases, L-glycine for gly-gly endopeptidases) using a DNFB assay), all three of these assays based on Petit, et al. (1966) "Peptide cross-links in bacterial cell wall peptidoglycans studied with specific endopeptidases from *Streptomyces albus* G" *Biochemistry* 5:2764-76; PMID: 5968582. Gly-gly endopeptidase activity can also be measured as the release of free amino groups from N-acetylated hexaglycine (acetyl-Gly6), see Kline, et al. (1994) "A colorimetric microtiter plate assay for lysostaphin using a hexaglycine substrate" *Anal. Biochem.* 217:329-331; PMID: 8203764.

Linker features may be tested to compare the effects on binding or catalysis of particular linkers, or to compare the various orientations of fragments. Panels of targets may be screened for catalytic fragments which act on a broader or narrower spectrum of target bacteria, and may include other microbes which may share cell wall components, e.g., mycobacteria or spores. This may make use of broader panels of related *Staphylococcus* strains, e.g., including *carnosus, epidermidis, simulans*, and *lentis* isolates. Strategies may be devised which allow for screening of larger numbers of candidates or variants.

One method to test for a cell wall degrading activity is to treat the phage with mild detergents or denaturants to release structurally associated proteins. These proteins are further tested for wall degrading or "lytic" activity on bacterial cells. Another method is to check for cell wall degradation activity or lysis from without (LO) on a phage resistant bacterial host. A third method to assess wall degrading or "lytic" activity associated with phage structural component is to perform Zymogram assays, e.g., where a pure phage preparation is electrophoresed on SDS-polyacrylamide gel incorporating autoclaved host bacteria cells. Proteins on the gels are allowed to renature in situ and then act upon the cell wall components giving rise to clear "lytic" zones when the rest of the gel stains blue with methylene blue dye. See, e.g., Lepeuple, et al, (1998) "Analysis of the bacteriolytic enzymes of the autolytic *lactococcus* lactis subsp. *cremoris* strain AM2 by renaturing polyacrylamide gel electrophoresis: identification of a prophage-encoded enzyme" *Appl. Environ. Microbiol.* 64:4142-428, PMID: 9797258. The clear zones are visualized and the protein band from the zones eluted, and identity determined, e.g., by N-terminal sequencing or by Mass spec. ORFs encoding the proteins can then be isolated.

VIII. Isolation of Nucleic Acids Encoding Cell Wall Degradative or Binding Polypeptides Nucleic acids have been identified that encode the cell wall "lytic" or binding proteins described above, e.g., Staph phages K, Twort, G1, or phi11, and conservatively modified variants of those sequences. The encoded cell wall "lytic" proteins have cell wall degrading activity, and those encoding identified CHAP domains are prime candidates, especially those where the CHAP domains are C proximal. Alternative sources include phage tail-like structures (e.g., pyocins or defective phage-like particles), or genomic sequences which possess characteristic features of "lytic" activity containing elements, e.g., which exhibit the gene organization characteristic of such structures (see, e.g., Rybchin (1984) "Genetics of bacteriophage phi 80—a review" *Gene* 27:3-11; PMID: 6232171).

Examples of nucleic acids that encode cell wall "lytic" polypeptides are also relevant to the nucleic acid embodiments of the invention. Methods of obtaining such nucleic acids will be recognized by those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). Besides synthetic methodologies, a wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook, et al. (1989) *Molecular Cloning—A Laboratory Manual* (2nd ed.) Vol. 1-3, Cold Spring Harbor Laboratory, Cold Spring Harbor Press, NY, (Sambrook, et al.); *Current Protocols in Molecular Biology*, Ausubel, et al., eds., *Current Protocols*, a joint venture between Greene Publishing Associates, Inc. and John Wiley & Sons, Inc., (1994 Supplement) (Ausubel); Cashion, et al., U.S. Pat. No. 5,017,478; and Carr, European Patent No. 0,246,864.

A DNA that encodes a cell wall degrading polypeptide, can be prepared by a suitable method described above, including, e.g., cloning and restriction of appropriate sequences with restriction enzymes. In one preferred embodiment, nucleic acids encoding cell wall degrading polypeptides are isolated by routine cloning methods. A nucleotide sequence of a cell wall degrading polypeptide as provided, e.g., in Accession Number YP_024486, can be used to provide probes that specifically hybridize to a gene encoding the polypeptide; or to an mRNA, encoding a cell wall degrading protein, in a total RNA sample (e.g., in a Southern or Northern blot). Once the target nucleic acid encoding a cell wall "lytic" protein is identified, it can be isolated according to standard methods known to those of skill in the art (see, e.g., Sambrook, et al. (1989) *Molecular Cloning: A Laboratory Manual* (2d ed., Vols. 1-3) Cold Spring Harbor Laboratory; Berger and Kimmel (1987) *Methods in Enzymology*, Vol. 152: *Guide to Molecular Cloning Techniques*, San Diego: Academic Press, Inc.; or Ausubel, et al. (1987) *Current Protocols in Molecular Biology*, Greene Publishing and Wiley-Interscience, New York). Further, the isolated nucleic acids can be cleaved with restriction enzymes to create nucleic acids encoding the full-length cell wall degrading polypeptide, or subsequences thereof, e.g., containing subsequences encoding at least a subsequence of a catalytic domain of a cell wall degrading polypeptide. These restriction enzyme fragments, encoding a cell wall degrading polypeptide or subsequences thereof, may then be ligated, for example, to produce a nucleic acid encoding a cell wall degrading polypeptide.

Similar methods can be used to generate appropriate cell wall binding fragments or linkers between fragments. Binding segments with affinity to prevalent surface features on target bacteria can be identified and include those from, e.g., phage K ORF56, *S. simulans* lysostaphin. L54a amidase, phage phi11 amidase, *S. aureus* lysostaphin analogue ALE-1 (see GI:3287732); bacterial SH3 domain segments found in *Staph. aureus* NCTC 8325 autolysin (see YP_500516), *Staph. aureus* JH9 N-acetylmuramoyl-L-alanine amidase family 2 (see ZP_01242312), *Staph. aureus* Mu50 amidase (see NP_371437), *Staph. aureus* RF122 phage-related amidase (see YP_417165), *Staph. aureus* peptidoglycan hydrolase (see AAA26662), *Staph. haemolyticus* JCSC1435 N-acetylmuramoly-L-alanine amidase (see YP_254248), *Staph. simulans* protein product CAA29494, bacterial peptidoglycan recognition proteins (PGRPs or PGLYRPs, a large family of highly conserved proteins found from insects to mammals that bind to bacterial peptidoglycan (PGN) of Gram-positive and Gram-negative bacteria), and other related sequences, e.g., homologues by sequence or location in gene cassettes. Bacterial cell walls of various species have been characterized, and proteins which bind thereto often are reported, e.g., in PubMed. Often the binding proteins will possess prokaryotic counterparts of the Sarc Homology 3 domains (SH3). Linker segments of appropriate lengths and properties can be used to connect binding and catalytic domains. See, e.g., Bae, et al. (2005) "Prediction of protein interdomain linker regions by a hidden Markov model" *Bioinformatics* 21:2264-2270; and George and Hering a (2003) "An analysis of protein domain linkers: their classification and role in protein folding" *Protein Engineering* 15:871-879.

A nucleic acid encoding an appropriate polypeptide, or a subsequence thereof, can be characterized by assaying for the expressed product. Assays based on the detection of the physical, chemical, or immunological properties of the expressed polypeptide can be used. For example, one can identify a cell wall degrading polypeptide by the ability of a polypeptide encoded by the nucleic acid to degrade or digest bacterial cells, e.g., as described herein.

Also, a nucleic acid encoding a desired polypeptide, or a subsequence thereof, can be chemically synthesized. Suitable methods include the phosphotriester method of Narang, et al. (1979) *Meth. Enzymol.* 68: 90-99; the phosphodiester method of Brown, et al. (1979) *Meth. Enzymol.* 68:109-151; the diethylphosphoramidite method of Beaucage, et al. (1981) *Tetra. Lett.* 22:1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding a desired polypeptide, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired polypeptide or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the cell wall degrading polypeptide or a polypeptide subsequence thereof by site-directed mutagenesis. The plasmid containing a cell wall degrading polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis, et al. (1987) U.S. Pat. No. 4,683,202; *PCR Protocols A Guide to Methods and Applications* (Innis, et al., eds) Academic Press Inc.

San Diego, Calif. (1990) (Innis); Arnheim and Levinson (Oct. 1, 1990) *C&EN* 36-47; *The Journal Of NIH Research* (1991) 3:81-94; (Kwoh, et al. (1989) *Proc. Nat'l Acad. Sci. USA* 86:1173; Guatelli, et al. (1990) *Proc. Nat'l Acad. Sci. USA* 87:1874; Lomeli, et al. (1989) *J. Clin. Chem.* 35:1826;

Landegren, et al., (1988) *Science* 241:1077-1080; Van Brunt (1990) *Biotechnology* 8: 291-294; Wu and Wallace (1989) *Gene* 4: 560; and Barringer, et al. (1990) *Gene* 89:117.

Some nucleic acids encoding cell wall degrading polypeptides can be amplified using PCR primers based on the sequence of the identified polypeptides.

Other physical properties, e.g., of a recombinant cell wall degrading polypeptide expressed from a particular nucleic acid, can be compared to properties of known desired polypeptides to provide another method of identifying suitable sequences or domains, e.g., of the cell wall degrading proteins that are determinants of bacterial specificity, binding specificity, and/or catalytic activity. Alternatively, a putative cell wall degrading polypeptide encoding nucleic acid or recombinant cell wall "lytic" polypeptide gene can be mutated, and its role as a cell wall degrading polypeptide, or the role of particular sequences or domains established by detecting a variation in bacterial "lysis" normally enhanced by the unmutated, naturally-occurring, or control cell wall degrading polypeptide. Those of skill will recognize that mutation or modification of cell wall degrading polypeptides of the invention can be facilitated by molecular biology techniques to manipulate the nucleic acids encoding the polypeptides, e.g., PCR. Other mutagenesis or gene shuffling techniques may be applied to the functional fragments described herein, including wall degrading activities, wall binding properties, or linker features compatible with chimeric constructs.

Functional domains of newly identified cell wall degrading polypeptides can be identified by using standard methods for mutating or modifying the polypeptides and testing them for activities such as acceptor substrate activity and/or catalytic activity, as described herein. The sequences of functional domains of the various cell wall degrading proteins can be used to construct nucleic acids encoding or combining functional domains of one or more cell wall degrading polypeptides. These multiple activity polypeptide fusions can then be tested for a desired bactericidal or bacteriostatic activity. Related sequences based on homology to identified "lytic" activities may be identified and screened for activity on appropriate substrates. Phage gene organization features characteristic of the polypeptides found on phage structures used to attach and penetrate target cell wall structures, e.g., cassette structures, may identify new sequences which may possess binding and/or bactericidal or bacteriostatic activities useful in attacking the wall from outside. Particular examples may include prophage sequences, including incomplete remnants of functional phage genomes, or pyocin-like structures, including particles derived from phage-like genetic segments, e.g., deletion or mutated genetic remnants of phage remaining in the DNA of a bacterium.

In an exemplary approach to cloning nucleic acids encoding cell wall degrading polypeptides, the known nucleic acid or amino acid sequences of cloned polypeptides are aligned and compared to determine the amount of sequence identity between them. This information can be used to identify and select polypeptide domains that confer or modulate cell wall degrading polypeptide activities, e.g., target bacterial or binding specificity and/or degrading or "lytic" activity based on the amount of sequence identity between the polypeptides of interest. For example, domains having sequence identity between the cell wall degrading polypeptides of interest, and that are associated with a known activity, can be used to construct polypeptides containing that domain and other domains, and having the activity associated with that domain (e.g., bacterial or binding specificity and/or wall degrading activity). Similar strategies may be applied to isolate bacterial SH3 domains which bind to cell wall structures, peptidoglycan recognizing proteins (PGRPs), phage tail "lytic" polypeptides, or to linkers for spacing between domains.

IX. Expression of Desired Polypeptides in Host Cells

Cell wall degrading, or other, proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debwyomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*.

Once expressed in a host cell, the cell wall degrading polypeptides can be used to prevent growth of appropriate bacteria. In a preferred embodiment, an ORF56 polypeptide is used to decrease growth of a *Staphylococcus* bacterium. In a further preferred embodiment, the protein is used to decrease growth of an *S. aureus* bacterium, or other similar *Staphylococcus* species. Fusion constructs combining such fragments may be generated, including fusion proteins comprising a plurality of wall degrading activities, including both peptidase and amidase catalytic activities (which may cleave both gly-gly and gly-ala linkages), or combining the activity with a targeting segment which binds to cell wall structures. Combinations of degrading activities may act synergistically to effect better bacteristatic or bactericidal activity. A linker may be incorporated to provide additional volume for catalytic sites of high local concentration near the binding target.

Typically, a polynucleotide that encodes the cell wall degrading polypeptides is placed under the control of a promoter that is functional in the desired host cell. An extremely wide variety of promoters is well known, and can be used in expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins, e.g., combining a catalytic fragment with a binding fragment, are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change, et al. (1977) *Nature* 198:1056), the tryptophan (bp) promoter system (Goeddel, et al. (1980) *Nucleic Acids Res.* 8:4057), the tac promoter (DeBoer, et al. (1983) *Proc. Nat'l Acad. Sci. USA* 80:21-25); and the lambda-derived $P_L$ promoter and N-gene ribosome binding site (Shimatake, et al. (1981) *Nature* 292: 128). The particular promoter system is typically not critical to the invention, many available promoters that function in prokaryotes can be used. A bacteriophage T7 promoter is used in various examples.

For expression of cell wall degrading polypeptides in prokaryotic cells other than *E. coli*, a promoter that functions in the particular prokaryotic production species is used. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An exemplary RBS in *E. coli* consists of a nucleotide sequence 3-9 nucleotides in length located 3-11 nucleotides upstream of the initiation codon (Shine and Dalgarno (1975) *Nature* 254:34; Steitz in Goldberger (ed. 1979) *Biological regulation and development: Gene expression* (vol. 1, p. 349) Plenum Publishing, NY).

For expression of proteins in yeast, convenient promoters include GAL1-10 (Johnson and Davies (1984) *Mol. Cell. Biol.* 4:1440-1448) ADH2 (Russell, et al. (1983) *J. Biol. Chem.* 258:2674-2682), PHO5 (*EMBO J.* (1982) 6:675-680), and MFα (Herskowitz and Oshima (1982) in Strathern, et al. (eds.) *The Molecular Biology of the Yeast Saccharomyces* Cold Spring Harbor Lab., Cold Spring Harbor, N.Y., pp. 181-209). Another suitable promoter for use in yeast is the ADH2/GAPDH hybrid promoter as described in Cousens, et al. (1987) *Gene* 61:265-275 (1987). For filamentous fungi such as, for example, strains of the fungi *Aspergillus* (McKnight, et al., U.S. Pat. No. 4,935,349), examples of useful promoters include those derived from *Aspergillus nidulans* glycolytic genes, such as the ADH3 promoter (McKnight, et al. (1985) *EMBO J.* 4:2093-2099) and the tpiA promoter. An example of a suitable terminator is the ADH3 terminator (McKnight, et al.).

Either constitutive or regulated promoters can be used in the present invention. Regulated promoters can be advantageous because the host cells can be grown to high densities before expression of the fusion proteins is induced. High level expression of heterologous polypeptides slows cell growth in some situations. An inducible promoter is a promoter that directs expression of a gene where the level of expression is alterable by environmental or developmental factors such as, for example, temperature, pH, anaerobic or aerobic conditions, light, transcription factors, and chemicals. Such promoters are referred to herein as "inducible" promoters, which allow one to control the timing of expression of the desired polypeptide. For *E. coli* and other bacterial host cells, inducible promoters are known to those of skill in the art. These include, for example, the lac promoter, the bacteriophage lambda $P_L$ promoter, the hybrid trp-lac promoter (Amann, et al. (1983) *Gene* 25:167; de Boer, et al. (1983) *Proc. Nat'l Acad. Sci. USA* 80:21), and the bacteriophage T7 promoter (Studier, et al. (1986) *J. Mol. Biol.*; Tabor, et al. (1985) *Proc. Nat'l Acad. Sci. USA* 82:1074-78). These promoters and their use are discussed in Sambrook, et al., supra.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication.

The construction of polynucleotide constructs generally requires the use of vectors able to replicate in bacteria. A plethora of kits are commercially available for the purification of plasmids from bacteria (see, e.g., EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a polypeptide, necessary for the survival or growth of transformed host cells grown in a selective culture medium. Host cells not transformed with the vector containing the selection gene will not survive in the culture medium. Typical selection genes encode polypeptides that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook, et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques Methods in Enzymology*, Volume 152, Academic Press, Inc., San Diego, Calif. (Berger); and *Current Protocols in Molecular Biology*, Ausubel, et at, eds., *Current Protocols*, a joint venture between Greene Publishing Associates, Inc. and John Wiley & Sons, Inc. (1998 Supplement) (Ausubel).

A variety of common Vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adenovirus, and baculovirus), episomal virus vectors (e.g., bovine papillomavirus), and retroviral vectors (e.g., murine retroviruses).

The methods for introducing the expression vectors into a chosen host cell are typically standard, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et al. (1988) *J. Biol. Chem.* 263: 16297-16302.

The various polypeptides of the invention can be expressed intracellularly, or can be secreted from the cell. Intracellular expression often results in high yields. If necessary, the amount of soluble, active fusion polypeptide may be increased by performing refolding procedures (see, e.g., Sambrook, et al., supra; Marston, et al. (1984) *Bio/Technology* 2:800; Schoner, et al. (1985) *Bio/Technology* 3:151). In embodiments in which the desired polypeptide are secreted from the cell, either into the periplasm or into the extracellular medium, the DNA sequence is often linked to a cleavable signal peptide sequence. The signal sequence directs translocation of the fusion polypeptide through the cell membrane. An example of a suitable vector for use in *E. coli* that contains a promoter-signal sequence unit is pTA1529, which has the *E. coli* phoA promoter and signal sequence (see, e.g., Sambrook, et al., supra; Oka, et at (1985) *Proc. Nat'l Acad. Sci. USA* 82:7212; Talmadge, et at (1980) *Proc. Nat'l Acad. Sci. USA* 77:3988; Takahara, et al. (1985) *J. Biol. Chem.* 260:2670). In another embodiment, the fusion polypeptides are fused to a subsequence of protein A or bovine serum albumin (BSA), for example, to facilitate purification, secretion, or stability. Affinity methods, e.g., using the target of the binding fragment may be appropriate.

The cell wall degrading polypeptides of the invention can also be further linked to other bacterial polypeptide segments, e.g., targeting fragments. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook, et al., supra). For certain applications, it may be desirable to cleave extraneous sequence from the fusion polypeptide after purification. This can be accomplished by any of several methods known in the art, including cleavage by cyanogen bromide, a protease, or by Factor $X_a$ (see, e.g., Sambrook, et al., supra; Itakura, et al. (1977) *Science* 198:1056; Goeddel, et al. (1979) *Proc. Nat'l Acad. Sci. USA* 76:106; Nagai, et al. (1984) *Nature* 309:810; Sung, et al. (1986) *Proc. Nat'l Acad. Sci. USA* 83:561). Cleavage sites can be engineered into the gene for the fusion polypeptide at the desired point of cleavage.

More than one recombinant polypeptide may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller, et al. (1989) *Biotechnology* 7:698-704. In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

X. Purification of Desired Polypeptides

The polypeptides of the present invention can be expressed as intracellular proteins or as proteins that are secreted from the cell, and can be used in this form, in the methods of the present invention. For example, a crude cellular extract containing the expressed intracellular or secreted polypeptides can be used in the methods of the present invention.

Alternatively, the polypeptides can be purified according to standard procedures of the art, including ammonium sulfate precipitation, affinity columns, column chromatography, gel electrophoresis and the like (see, generally, Scopes (1982) *Protein Purification* Springer-Verlag, N.Y.; Deutscher (1990) *Methods in Enzymology* (vol. 182) *Guide to Protein Purification*, Academic Press, Inc. NY). Because the degrading segments, at least, derive from phage proteins selected for stability, purification may make use of these properties to denature contaminating materials. Substantially pure compositions of at least about 70, 75, 80, 85, 90% homogeneity are preferred, and about 92, 95, 98 to 99% or more homogeneity are most preferred. The purified polypeptides may also be used, e.g., as immunogens for antibody production, which antibodies may be used in immunoselection purification methods.

To facilitate purification of the polypeptides of the invention, the nucleic acids that encode them can also include a coding sequence for an epitope or "tag" for which an affinity binding reagent is available, e.g., a purification tag. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the polypeptides of the invention, and corresponding detection systems are known to those of skill in the art, and several are commercially available (e.g., FLAG, Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli "Purification of recombinant proteins with metal chelating adsorbents" in Setlow (ed. 1990) *Genetic Engineering: Principles and Methods*, Plenum Press, NY; commercially available from Qiagen (Santa Clarita, Calif.)). Purification tags also include maltose binding domains and starch binding domains. Purification of maltose binding domain proteins is known to those of skill in the art.

Other haptens that are suitable for use as tags are known to those of skill in the art and are described, for example, in the *Handbook of Fluorescent Probes and Research Chemicals* (6th ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that certain modifications can be made to the catalytic or functional domains of the polypeptide without diminishing their biological activity. Some modifications may be made to facilitate the cloning, expression, or incorporation of the catalytic domain into a fusion polypeptide. Such modifications are well known to those of skill in the art and include, for example, the addition of codons at either terminus of the polynucleotide that encodes the catalytic domain, e.g., a methionine added at the amino terminus to provide an initiation site, or additional amino acids (e.g., poly His) placed on either terminus to create conveniently located restriction enzyme sites or termination codons or purification sequences.

It must be noted that as used herein and in the appended claims, the singular forms "a", "and", and "the" include plural referents unless the context clearly dictates otherwise. Thus, e.g., reference to "a bacteriophage" includes a plurality of such bacteriophage and reference to a "host bacterium" includes reference to one or more host bacteria and equivalents thereof known to those skilled in the art, and so forth.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference in their entirety.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

I. Full Length ORF56

Accession Number YP_024486 reported a putative ORF56 found in a *Staphylococcus* phage K. Based upon this report, a full length Phage K ORF56 was PCR amplified from an appropriate phage source. Using gene specific primers with an NdeI site in the forward primer and XhoI in the reverse primer, this PCR product was cloned into a pET21a vector under a T7 promoter as an NdeI-XhoI insert. This clone was labeled pGMB617 and contained the coding region corresponding to amino acids 1 to 808 of the expected product (SEQ ID NO:1), which should produce a protein product of about 91 kDa.

A. CHAP Domain

The report describing Accession Number YP_024486 identified a domain described as a Cysteine-Histidine dependent Aminohydrolase/Peptidase (CHAP). See, e.g., Rigden, et al. (2003) *Trends Biochem. Set.* 28:230-234. Certain genes recognized as containing lytic activities possess CHAP domains, generally with the domain at the N proximal region of the encoded polypeptides. The CHAP domain is on the C proximal region of the putative ORF56 and should correspond to the designated amino acids from about amino acids 690 to 805.

B. Degradation Product

However, after production and purification, protein products of approximately 50 kDa and approximately 23 kDa were present in substantial amounts as observed by PAGE. These appeared to represent stable degradation products of the original 91 kDa expressed protein.

II. *Staphylococcus* Target Species

Purified protein constructs were initially tested for decrease in CFU (colony forming units) on a *Staphylococcus aureus* isolate. Certain constructs were further tested for decrease in CFU on isolates of *S. epidermidis*, *S. lentis*, and *S. carnosus*. It appears that the lytic activities observed here are less strain specific than many phage infection selectivities. Thus, it is likely that use of the lytic activities described herein will also exhibit multiple strain specificities, and may even be broad across many genera or other functional or structural classes of bacteria, e.g., all Gram-positive or even including some or all Gram-negative. Moreover, the lytic activities may also be generic to shared structural features between Gram-positive and Gram-negative classes. For example some features of Gram-negative inner bacterial cell walls may be shared with the Gram-positive cell walls.

III. Truncation Constructs

The region described as hypothetical ORF56 has a unique internal PstI site, whose use could easily generate a construct which would provide approximately 57 kDa of C terminal region of the protein from about amino acids 297 to 808 of SEQ ID NO:1. From the full length ORF56 clone described above, a PstI-HindIII fragment was excised encoding the C terminal portion of the reading frame. The PstI-HindIII fragment was cloned into a pRSETA vector generating pRSETA-57 kDa (pGMB 599) ORF56 clone construct. From this was excised an NdeI-HindIII fragment which was cloned into pET21a vector as NdeI-HindIII to generate pGMB 612. This clone expressed the 57 kDa protein (expected) as well as about 50 kDa and about 23 kDa proteins. The smaller proteins are, unexpectedly, apparently stable degradation products of about the same size as from the construct expressing the full length 91 kDa protein.

A DNA sequence was constructed to produce a 50 kDa C terminal portion of the putative ORF56 region corresponding to about amino acids 363 to 808 of SEQ ID NO:1. A PCR amplified product was generated using appropriate specific primers. The PCR product had an NdeI site in the forward primer and an XhoI site in the reverse primer, and the resulting NdeI-XhoI fragment was cloned into pET21a vector to incorporate an NdeI-XhoI insert. This product was labeled pGDC060/061. This construct expressed a protein of 50 kDa (as expected) and a protein of about 23 kDa. Again, the smaller protein is, unexpectedly, apparently a stable degraded ORF56 protein of about the same size as observed for the constructs of the full length 91 kDa ORF56 protein and the truncated 57 kDa ORF56 protein.

A DNA construct was generated to produce the 23 kDa C terminal portion of the ORF56 protein corresponding to about Met-(amino acid 603 to 808). DNA sequence of the ORF56 that codes for 23 kDa of the C terminal region was PCR amplified introducing an ATG start codon in the forward primer. The PCR product was cloned into pET21a as an NdeI-XhoI fragment to generate a construct labeled as pGDC070. This construct expressed proteins which run at about 27 kDa on SDS PAGE and another protein which runs at about 23 kDa. On storage at 4° C., the two forms collapse to a single band of about 23 kDa.

A DNA construct was generated to produce a 19 kDa C terminal fragment of the ORF56 protein corresponding to about amino acids 620 to 808. DNA sequence corresponding thereto was amplified using specific primers and cloned into pET21a as an NdeI-XhoI insert. The resulting construct was designated pGDC089. This construct expressed a single protein that ran on SDS PAGE at about 21 kDa, about the same as the stable degradation product observed from the constructs described above.

These various constructs suggest that the 91 kDa full length protein product is not particularly stable under the conditions used. Two reasonably stable degradation products appear, first a 50 kDa protein, and then a 23 kDa protein. The degradation, whether from a rapid exoprotease activity, from an endoprotease activity, or a combination of both is yet unclear. However, it does appear that the different constructs are degraded to a stable 23 kDa truncated ORF56 protein.

IV. Antimicrobial Activity of Purified Proteins

The various ORF56 truncations and/or degradation products were tested for lytic activity using an assay which determined the decrease in CFU (colony forming units) of *Staphylococcus aureus* bacterial cultures. In all cases, the ORF56 truncations or degradation products exhibited significant ability to decrease *S. aureus* CFU in solution, suggesting that the constructs and stable degradation products all retain lytic activity on cell walls. The common structural feature in all of the constructs is the C terminal region, including the CHAP domain.

V. Candidate Homologous Genes with Chap Domains to be Tested for Lytic Activity

ORF56 bactericidal activity correlated with the C-terminal CHAP domain. Therefore, a BLAST search was used to identify additional "lytic" activities in sequenced phage genomes. Other useful sources of these "lytic" segments include components involved in penetration of phage genome into hosts, e.g., derived from tails or binding components used by phage to attach to target hosts or from prophage or pyocin-like structures. Further so called "lytic" activities may be identified as being in coding segments for page tail cassettes, e.g., based upon characteristic gene organization.

The searches are done using the CHAP domain or other features. In particular, those genes where the CHAP domain is at the C-terminal region of the ORF are more likely to be relevant to this activity. Of particular interest are CHAP domain-containing proteins from Staphylococcal phages K, Twort, and G1.

VI. Chimeric Constructs

A number of fusion constructs were made linking a catalytic fragment which acts on the cell wall of target *Staph* strains to a targeting fragment which binds to a cell surface entity. The binding moiety provides selective localization to the surface of the appropriate target bacterium, and the catalytic activity acts on nearby substrate sites. A linker may be incorporated, allowing for a broader region of substrate accessibility (region of high active site concentration). Different binding moieties might be used which recognize highly accessible, highly expressed, or selective bacterial cell surface markers. Gram-negative cell wall marker binding segments may be found from proteins derived from host bacteria, and similar Gram-negative wall marker binding segments may be found from proteins used by them to control cell wall structure. Phage specific for the hosts should also have tail polypeptides which recognize and bind their respective host cell wall. Peptidoglycan recognition proteins (PGRPs) from sources ranging from low to higher eukaryotes and other binding proteins which bind with affinity to particular bacterial cell walls, preferably in physiological conditions and form, will be sources for appropriate binding activity fragments. On some circumstances, a plurality of different moieties might be employed. Linkers may be selected for ability to allow the other fragments to properly fold without interference while providing a tether to increase local catalytic concentration near appropriate substrates. Catalytic fragments may target preferred substrates, and a plurality of fragments may target different linkages found on target bacteria.

In particular, addressing Gram-positive targets, binding segments would preferably originate from proteins which recognize the extracellular cell wall as "exhibited" physiologically by the bacteria. Thus, proteins which recognize Gram-negative cell walls may include immune system components which recognize these infectious agents. An appropriate source for the cell wall degrading domains will be tail structures from phage which infect Gram-negative hosts. Likewise, for Gram-positive, binding domains can derive from tail structures from Gram-positive infecting phage or from the PGRPs for Gram-negative bacteria. The wall degrading activities may be derived from tail structures that infect Gram-negative hosts. To the extent that mycobacteria, spores, or other prokaryote or related organisms share the structure of the cell wall, these reagents may be useful to modulate their growth.

In addition, because of the selection processes for phage which infect particular hosts, phage which target hosts which live in extreme conditions, thermophiles, halophiles, conditions of high oxidation or reactive species, pH extremes, highly proteolytic environments, and the like are particularly interesting sources for useful catalytic or binding fragments. The proteins which are exposed to the external environment outside the cell (yearning to enter) must have highly evolved features to survive outside the relatively safe intracellular environment. As such, this stability to hostile conditions will select for structural features of the domain which will provide great stability for the product. And the product should have good storage properties, may be selected for pharmacological survival and lifetime, and may provide simple means for purification and isolation.

Constructs were made comprising various segments from the ORF56 sequence (see GeneID 2948023, YP_024486, YP_024486.1); the 16 KDa fragment corresponding to aa669-808; 19 KDa fragment corresponding to aa629-808; 13 KDa fragment corresponding to aa691-808; and ORF56 binding fragment corresponding to aa629-690. *Staphylococcus* lysostaphin (lss; AAB53783) segments include the binding fragment corresponding to aa395-493; and catalytic (lys-lys cleavage) fragment corresponding to aa248-394. An L54a amidase (AAW38858; YP_185281) binding fragment corresponds to aa376-484. A LytM peptidase (L77194; AAV62278.1) catalytic fragment corresponds to aa223-322. A phage phi11 amidase (NP_803306; AAL82281; see 40893-42365 of AF424781.1) fragment corresponds to aa391-490. The constructs were driven by a T7 promoter.

A number of fusion constructs were made: Construct 1 has the sequence Met-(16 KDa ORF56 catalytic fragment)-Leu- Glu-(lysostaphin binding fragment) and the resulting protein product is referred to as chimera 128 (SEQ ID NO:4). Construct 2 has the sequence (19 KDa ORF56 catalytic fragment)-Leu-Glu-(lysostaphin binding fragment). Construct 3 has the sequence (13 KDa ORF56 catalytic fragment)-Leu-Glu-(lysostaphin binding fragment). Construct 4 has the sequence (16 KDa ORF56 catalytic fragment)-Leu-Glu-(L54a amidase binding fragment). Construct 5 has the sequence Met-(LytM peptidase catalytic fragment)-Leu-Glu-(lysostaphin binding fragment). Construct 6 has the sequence Met-(lysostaphin catalytic fragment)-(ORF56 binding fragment). Construct 7 has the sequence (LytM peptidase catalytic fragment)-Construct I, which has two catalytic domains (LytM peptidase, ORF56). Construct 8 has the sequence Met-16 KDa ORF56 catalytic fragment-Leu-Glu-(phi11 amidase binding fragment). Likewise, other catalytic or binding fragments from other sources may be used, or variants of these may be generated and optimized for desired features.

The construct 1 was produced in the appropriate host, and the host lysed including a sonication step. Similar methods are applied for the other constructs. The crude lysate was purified by ammonium sulfate precipitation (20-50%), Q-500 column chromatography (pH 7.5), CM cellulose chromatography (pH 6.0) using 200 mM NaCl for elution, and gel filtration. The product was estimated to be >98% pure by silver staining.

VII. Activity Testing

The construct 1 product, chimera 128, was tested on a panel of 30 distinct typed *Staphylococcus aureus* strains, selected for spa, Agr, or Mec types, and including MLST and methicillin resistance. Chimera 128 was active on these tested strains, and lawn inhibition was observed with spotting of 1.5 microgram of protein. Using an MRSA strain B911 at about 1E8 CFU, full length ORF56 protein at 50 microgram decreased CFU about 2 log units, while chimera 128 at 1.5 microgram reduced CFU by about 5 log units (10,000 fold). On various representative strains of *Staph. aureus* at 5E5 cells/ml in Mueller Hinton Broth containing 1% BSA (see Kusuma and Kokai-Kun (2005) "Comparison of four methods for determining lysostaphin susceptibility of various strains of *Staphylococcus aureus*" Antimicrob. Agents Chemother. 49:3256-263; PMID: 16048934) incubated at 35° C., colonies were static for 16 hr. The minimum inhibitory concentration (MIC) for chimera 128 was about 1-10 microgram/ml. Testing of survivors of the *S. aureus* COL strain to a first exposure with chimera 128 was tested and survivors were found to be sensitive to protein at reexposure. Testing of a lysostaphin-resistant variant of *S. aureus* strain B911 showed that 99.9% of the cells were to 1.5 microgram of chimera 128 protein.

The chimera 128 is stable in Tris buffer at 4° C. for at least a month, about 4 weeks at room temperature (about 25° C.), and about 1 day at 37° C. Certain gel and liquid formulations had much longer lengths of stability.

Additional chimera constructs were tested for activity using lawn inhibition assays, zymogram assays, and colony forming unit (CFU) drop assays. A lawn inhibition assay is a qualitative assay where test proteins are spotted onto a lawn of bacteria and growth inhibition zones are measured. Bactericidal activity corresponds to a zone of inhibition on the lawn; no activity corresponds to no visible inhibition zone. A zymogram assay is also a qualitative assay where an SDS-PAGE gel is impregnated with autoclaved target bacterial cells and a phage preparation is electrophoresed through the gel. Proteins on the gels are allowed to renature in situ and then act upon the cell wall components giving rise to clear "lytic" zones after staining the gel with methylene blue dye. See, e.g., Lepeuple, et al. (1998) Appl. Environ. Microbiol. 64:4142428, PMID: 9797258. Activity corresponds to visible clear zones against a dark blue background. The CFU drop assay is a quantitative assay where activity is measured by the percentage killing. Bacterial cultures are mixed with chimera proteins and plated onto LB medium. Activity corresponds to reduction in cell numbers by at least 99.9%. No activity corresponds to no reduction in cell numbers. Appropriate positive and negative controls are performed with each assay. Results for a number of chimeric proteins are shown in Table 1. Activity was demonstrated for a number of TAME-CBD proteins that comprised an ORF56 muralytic domain, also reffered to as a catalytic domain (CD). A TAME-CBD protein that comprised Lysostaphin CD and an ORF56 binding domain also had bactericidal activity.

TABLE 1

| CHIMERA | Lawn inhibition | Zymogram | CFU drop assay |
| --- | --- | --- | --- |
| 16 kDa ORF56- Lysostaphin BD | Active | Active | Active |
| 19 kDa ORF56-LysostaphinBD | Active | Active | Active |
| 16 kDa ORF56- Lys17 BD | No activity | No activity | No activity |
| 16 kDa ORF56- L54a amidase BD | Active | Active | No activity |
| 13 kDa ORF56- Lysostaphin BD | No activity | No activity | No activity |
| LytM peptidase- 16 kDa ORF56- Lysostaphin BD | Active | Active | Active |
| Lysostaphin CD- ORF56 BD fusion | Active | Active | — |

Identification of TAME Conserved Domains

We have developed a comprehensive strategy to identify TAME genes in Caudovirales phage genomes. To look for candidate TAME genes, we rely on the presence in each TAME of a conserved domain (CD) associated with bacterial cell wall binding, a binding domain (CBD) or degradation, muralytic domain (MD). FIG. 1 is an exemplary list of such domains we have generated from a search of the NCBI CDD (Conserved Domain Database) at its website ncbi.nlm.nih.gov/Structure/cdd/cdd.shtml, using the following search keyword string: "lysozyme OR endolysin OR lysin OR muramidase OR muraminidase OR glucosaminidase OR murein OR peptidoglycan OR cell wall OR lysis OR amidase OR transglycosylase OR autolysin OR hydrolase". Those of skill will recognize that a variety of search strategies using different search terms can be performed. Other databases, can also be searched.

The search product Was then manually inspected for relevance to bacterial cell wall binding, maintenance or degradation. A non-limiting list of Conserved Domains associated with bacterial cell wall binding function (abbreviated CBD for cell binding domain) or degrading function (abbreviated MD for muralytic domain) follows. Any of the conserved domains listed below can be used in any combination to generate a bactericidal chimeric TAME-CBD protein of the invention.

pfam05382: Amidase_5: Bacteriophage peptidoglycan hydrolase. At least one of the members of this family, the Pal protein from the pneumococcal bacteriophage Dp-1 has been shown to be a N-acetylmuramoyl-L-alanine amidase. According to the known modular structure of this and other peptidoglycan hydrolases from the pneumococcal system, the active site should reside at the N-terminal domain whereas the C-terminal domain binds to the choline residues of the cell wall teichoic acids. This family appears to be related to pfam00877. [pfam05382|68934]. MD pfam01510: Amidase_2: N-acetylmuramoyl-L-alanine amidase. This family includes zinc amidases that have N-acetylmuramoyl-L-alanine amidase activity EC:3.5.1.28. This enzyme domain cleaves the amide bond between N-acetylmuramoyl and L-amino acids in bacterial cell walls (preferentially: D-lactyl-L-Ala). The structure is known for the bacteriophage T7 structure and shows that two of the conserved histidines are zinc binding. [pfam01510|65318]. MD pfam01520: Amidase_3: N-acetylmuramoyl-L-alanine amidase. This enzyme domain cleaves the amide bond between N-acetylmuramoyl and L-amino acids in bacterial cell walls. [pfam01520|65327]. MD pfam00912: Transgly: Transglycosylase. The penicillin-binding proteins are bifunctional proteins consisting of transglycosylase and transpeptidase in the N- and C-terminus respectively. The transglycosylase domain catalyses the polymerization of murein glycan chains. [pfam00912|64762]. MD cd00737: endolysin_autolysin: Endolysins and autolysins are found in viruses and bacteria, respectively. The ds DNA phages of eubacteria use endolysins or muralytic enzymes in conjunction with hollin, a small membrane protein, to degrade the peptidoglycan found in bacterial cell walls. Similarly, bacteria produce autolysins to facilitate the biosynthesis of its cell wall hetropolymer peptidoglycan and cell division. Both endolysin and autolysin enzymes cleave the glycosidic beta 1,4-bonds between the N-acetylmuramic acid and the N-acetylglucosamine of the peptidoglycan. [cd00737|29561]. MD pfam07486: Hydrolase_2: Cell Wall Hydrolase. These enzymes have been implicated in cell wall hydrolysis, most extensively in Bacillus subtilis. For instance Bacillus subtilis SCLE, the spore cortex-lytic enzyme is expressed during sporulation as an inactive form and then deposited on the cell outer cortex. During germination the enzyme is activated and hydrolyses the cortex. A similar role is carried out by the partially redundant cell wall hydrolase cw1.1. These enzymes may be amidases or peptidases. [pfam07486|70935]. MD pfam05257: CHAP domain. This domain corresponds to an amidase function. Many of these proteins are involved in cell wall metabolism of bacteria. This domain is found at the N-terminus of a bifunctional Escherichia coli enzyme, where is functions as a glutathionylspermidine amidase EC:3.5.1.78. [pfam05257|68816] ORF56 provides an example of a CHAP domain. MD pfam03562: MltA: MltA specific insert domain. This beta barrel domain is found inserted in the MltA a murein degrading transglycosylase enzyme. This domain may be involved in peptidoglycan binding. [pfam03562|67195]. MD pfam01471: PG_binding_1: Putative peptidoglycan binding domain. This domain is composed of three alpha helices. This domain is found at the N or C terminus of a variety of enzymes involved in bacterial cell wall degradation. This domain may have a general peptidoglycan binding function. This family is found N-terminal to the catalytic domain of matrixins. [pfam01471|65280] CBD pfam08823: PG_binding_2: Putative peptidoglycan binding domain. This family may be a peptidoglycan binding domain. [pfam08823|72246] CBD pfam06737: Transglycosylase: Transglycosylase-like domain. This family of proteins are very likely to act as transglycosylase enzymes related to pfam00062 and pfam01464. These other families are weakly matched by this family, and include the known active site residues. [pfam06737|70216]. MD pfam06267: DUF1028: Family of unknown function (DUF1028). Family of bacterial and archaeal proteins with unknown function. Some members are associated with a C-terminal peptidoglycan binding domain and may be involved in peptidoglycan metabolism. [pfam06267|69772]. CBD and MD pfam01476: LysM: LysM domain. The LysM (lysin motif) domain is about 40 residues long. It is found in a variety of enzymes involved in bacterial cell wall degradation. This domain may have a general peptidoglycan binding function. The structure of this domain is known. [pfam01476|65285]. CBD smart00701: PGRP: Animal peptidoglycan recognition proteins homologous to Bacteriophage T3 lysozyme. The bacteriophage molecule, but not its moth homologue, has been shown to have N-acetylmuramoyl-L-alanine amidase activity. One member of this family, Tag7, is a cytokine. [smart00701|47970]. CBD COG2951: MltB: Membrane-bound lytic murein transglycosylase 13 [Cell envelope biogenesis, outer membrane] [COG2951|32773]. MD COG2821: MltA: Membrane-bound lytic murein transglycosylase [Cell envelope biogenesis, outer membrane] [COG2821|32649]. MD COG0741: MltE: Soluble lytic murein transglycosylase and related regulatory proteins (some contain LysM/invasin domains) [Cell envelope biogenesis, outer membrane] [COG0741|31084]. MD cd00736: bacteriophage_lambda_lysozyme: The lysozyme from bacteriophage lambda hydrolyses the beta-1, 4-glycosidic bond between N-acetylmuramic acid (MurNAc) and N-acetylglucosamine (GlcNAc), as do other lysozymes. But unlike other lysozymes, bacteriophage lambda does not produce a reducing end upon cleavage of the peptidoglycan but rather uses the 6-OH of the same MurNAc residue to produce a 1,6-anhydromuramic acid terminal residue and is therefore a lytic transglycosylase. An identical 1,6-anhydro bond is formed in bacterial peptidoglycans by the action of the lytic transglycosylases of E. coli. However, they differ structurally. [cd00736|29560]. MD cd00118: LysM: Lysin domain, found in a variety of enzymes involved in bacterial cell wall degradation. This domain may have a general peptidoglycan binding function. [cd00118|29017]. CBD pfam08230: Cpl-7: Cpl-7 lysozyme C-terminal domain. This domain was originally found in the C-terminal moiety of the Cpl-7 lysozyme encoded by the Streptococcus pneumoniae bacteriophage Cp-7. [pfam08230|71664] CBD and MD pfam03411: Peptidase_M74: Penicillin-insensitive murein endopeptidase. [pfam03411|67049] 22: pfam01473 CW_binding_1: Putative cell wall binding repeat. These repeats are characterised by conserved aromatic residues and glycines are found in multiple tandem copies in a number of proteins. The CW repeat is 20 amino acid residues long. These repeats in Streptococcus phage CP-1 lysozyme may be responsible for the specific recognition of choline-containing cell walls. Similar but longer repeats are found in the glucosyltransferases and glucan-binding proteins of oral streptococci and shown to be involved in glucan binding as well as in the related dextransucrases of Leuconostoc mesenteroides.

Repeats also occur in toxins of *Clostridium difficile* and other clostridia, though the ligands are not always known. [pfam01473|65282] CBD pfam01464: SLT: Transglycosylase SLT domain. This family is distantly related to pfam00062. Members are found in phages, type II, type III and type IV secretion systems (reviewed in). [pfam01464|65274]. MD pfam00062: Lys: C-type lysozyme/alpha-lactalbumin family. Alpha-lactalbumin is the regulatory subunit of lactose synthase, changing the substrate specificity of galactosyltransferase from N-acetylglucosamine to glucose. C-type lysozymes are secreted bacteriolytic enzymes that cleave the peptidoglycan of bacterial cell walls. Structure is a multi-domain, mixed alpha and beta fold, containing four conserved disulfide bonds. [pfam00062|63951]. MD COG5632: COG5632: N-acetylmuramoyl-L-alanine amidase [Cell envelope biogenesis, outer membrane] [COG5632|35191 MD COG5479: COG5479: Uncharacterized protein potentially involved in peptidoglycan biosynthesis [Cell envelope biogenesis, outer membrane] [COG5479|35038]. CBD and MD COG4623: COG4623: Predicted soluble lytic transglycosylase fused to an ABC-type amino acid-binding protein [Cell envelope biogenesis, outer membrane] [COG4623|34243]. CBD and MD COG3863: COG3863: Uncharacterized distant relative of cell wall-associated hydrolases [COG3863|33653]. CBD and MD COG3773: SleB: Cell wall hydrolyses involved in spore germination [Cell envelope biogenesis, outer membrane] [COG3773|33568]. CBD and MD COG3770: MepA: Murein endopeptidase [Cell envelope biogenesis, outer membrane] [COG3770|33565]. MD COG3409: COG3409: Putative peptidoglycan-binding domain-containing protein [Cell envelope biogenesis, outer membrane] [COG3409|33215]. CBD COG3023: ampD: N-acetyl-anhydromuramyl-L-alanine amidase [Cell envelope biogenesis, outer membrane] [COG3023|32839]. MD COG2247: LytB: Putative cell wall-binding domain [Cell envelope biogenesis, outer membrane] [COG2247|32428]. CBD COG1215: COG1215: Glycosyltransferases, probably involved in cell wall biogenesis [Cell envelope biogenesis, outer membrane] [COG 1215|31408]. CBD COG0860: AmiC: N-acetylmuramoyl-L-alanine amidase [Cell envelope biogenesis, outer membrane] [COG0860|31201]. MD COG0791: Spr: Cell wall-associated hydrolases (invasion-associated proteins) [Cell envelope biogenesis, outer membrane] [COG0791|31134]. MD cd02848: Chitinase_N_term: Chitinase N-terminus domain. Chitinases hydrolyze the abundant natural biopolymer chitin, producing smaller chito-oligosaccharides. Chitin consists of multiple N-acetyl-D-glucosamine (NAG) residues connected via beta-1,4-glycosidic linkages and is an important structural element of fungal cell wall and arthropod exoskeletons. On the basis of the mode of chitin hydrolysis, chitinases are classified as random, endo-, and exo-chitinases and based on sequence criteria, chitinases belong to families 18 and 19 of glycosyl hydrolases. The N-terminus of chitinase may be related to the immunoglobulin and/or fibronectin type III superfamilies. These domains are associated with different types of catalytic domains at either the N-terminal or C-terminal end and may be involved in homodimeric/tetrameric/dodecameric interactions. Members of this family include members of the alpha amylase family, sialidase, galactose oxidase, cellulase, cellulose, hyaluronate lyase, chitobiase, and chitinase. [cd02848|30335]. MD cd02847: Chitobiase_C_term: Chitobiase C-terminus domain. Chitobiase (AKA N-acetylglucosaminidase) digests the beta, 1-4 glycosidic bonds of the N-acetylglucosamine (NAG) oligomers found in chitin, an important structural element of fungal cell wall and arthropod exoskeletons. It is thought to proceed through an acid-base reaction mechanism, in which one protein carboxylate acts as catalytic acid, while the nucleophile is the polar acetamido group of the sugar in a substrate-assisted reaction with retention of the anomeric configuration. The C-terminus of chitobiase may be related to the immunoglobulin and/or fibronectin type III superfamilies. These domains are associated with different types of catalytic domains at either the N-terminal or C-terminal end and may be involved in homodimeric/tetrameric/dodecameric interactions. Members of this family include members of the alpha amylase family, sialidase, galactose oxidase, cellulase, cellulose, hyaluronate lyase, chitobiase, and chitinase. [cd02847|30334]. MD cd00735: bacteriophage_T4-like_lysozyme: Bacteriophage T4-like lysozymes hydrolyse the beta-1,4-glycosidic bond between N-acetylmuramic acid (MurNAc) and N-acetylglucosamine (GlcNAc) in peptidoglycan heteropolymers of prokaryotic cell walls. Members include a variety of bacteriophages (T4, RB49, RB69, Aeh1) as well as Dictyostelium. [cd00735|29559]. MD cd00254: LT_GEWL: Lytic Transglycosylase (LT) and Goose Egg White Lysozyme (GEWL) domain. Members include the soluble and insoluble membrane-bound LTs in bacteria, the LTs in bacteriophage lambda, as well as, the eukaryotic "goose-type" lysozymes (GEWL). LTs catalyze the cleavage of the beta-1,4-glycosidic bond between N-acetylmuramic acid (MurNAc) and N-acetyl-D-glucosamine (GlcNAc), as do "goose-type" lysozymes. However, in addition to this, they also make a new glycosidic bond with the C6 hydroxyl group of the same muramic acid residue. [cd00254|29556]. MD cd00119: LYZ1: C-type lysozyme (1,4-beta-N-acetylmuramidase, LYZ) and alpha-lactalbumin (lactose synthase B protein, LA). They have a close evolutionary relationship and similar tertiary structure, however, functionally they are quite different. Lysozymes have primarily bacteriolytic function; hydrolysis of peptidoglycan of prokaryotic cell walls and transglycosylation. LA is a calcium-binding metalloprotein that is expressed exclusively in the mammary gland during lactation. LA is the regulatory subunit of the enzyme lactose synthase. The association of LA with the catalytic component of lactose synthase, galactosyltransferase, alters the acceptor substrate specificity of this glycosyltransferase, facilitating biosynthesis of lactose. [cd00119|29018]. MD smart00047: LYZ2: Lysozyme subfamily 2; Eubacterial enzymes distantly related to eukaryotic lysozymes. [smart00047|47396]. MD pfam02016: Peptidase_S66: LD-carboxypeptidase. Muramoyl-tetrapeptide carboxypeptidase hydrolyses a peptide bond between a di-basic amino acid and the C-terminal D-alanine in the tetrapeptide moiety in peptidoglycan. This cleaves the bond between an L- and a D-amino acid. The function of this activity is in murein recycling. This family also includes the microcin c7 self-immunity protein. This family corresponds to Merops family S66. [pfam02016|65774]. MD pfam02324: Glyco_hydro_70: Glycosyl hydrolase family 70. Members of this family belong to glycosyl hydrolase family 70 Glucosyltransferases or sucrose 6-glycosyl transferases (GTF-S) catalyse the transfer of D-glucopyramnosyl units from sucrose onto acceptor molecules, EC:2.4.1.5. This family roughly corresponds to the N-terminal catalytic domain of the enzyme. Members of this family also contain the Putative cell wall binding domain pfam01473, which corresponds with the C-terminal glucan-binding domain. [pfam02324|66049]. MD pfam06347: SH3_4: Bacterial SH3 domain. This family consists of several hypothetical bacterial proteins of unknown function. These are composed of SH3-like domains. [pfam06347|69844]. CBD pfam08239: SH3_3: Bacterial SH3 domain. [pfam08239|71673]. CBD pfam08460: SH3_5: Bacterial SH3 domain. [pfam08460|71889]. CBD COG4991: COG4991: Uncharacterized protein with a bacterial SH3 domain homologue [COG4991|34596]. CBD COG3103: COG3103: SH3 domain protein [Signal transduction mechanisms] [COG3103|32917]. CBD smart00287: SH3b: Bacterial SH3 domain homologues; [smart00287|47616]. CBD pfam01551: Peptidase_M23: Peptidase family M23. Members of this family are zinc metallopeptidases with a range of specificities. The peptidase family M23 is included in this family, these are Gly-Gly endopeptidases. Peptidase family M23 are also endopeptidases. This family also includes some bacterial lipoproteins for which no proteolytic activity has been demonstrated. This family also includes leukocyte cell-derived chemotaxin 2 (LECT2) proteins. LECT2 is a liver-specific protein which is thought to be linked to hepatocyte growth although the exact function of this protein is unknown. [pfam01551|65358]. MD Method of Scanning of Phage Genomes for TAME Candidates Currently the process is done by manual inspection of each phage genome, although automated scanning may be implemented by CDD [Conserved Domain Database in NCBI; or its equivalent] in the future. The step by step process is listed below, using the *Stapholycoccus* phage 11 as an example.

1. Identify a phage genome in [appropriate database, e.g.,] the Genbank Phage Genomes database (ncbi.nlm.nih.gov/genomes/static/phg.html). Select its reference number (NC number to right of screen; for phage 11, it is NC_004615). [this description is based on using this database, on this date; as the look/feel design evolves, this description then becomes "exemplary"]

2. From the Genome Overview window, select the Protein Coding feature [or its functional equivalent] (in this case, 53 proteins). A window listing all of the predicted protein products of the genome will open, with the complete predicted protein list. In this case, the gene products have been extensively annotated; however, this method does not require a previous annotation, other than the automated identification of potential ORFs.

3. The next step is to examine each predicted protein product for the presence of one of the CDs [Conserved Domains; i.e., a cell binding domain or a muralytic domain] listed above. This manual examination should start with the largest predicted protein and proceed down the size list. In the case of phage 11 [by example], the largest ORF is phi11_45, predicted to encompass 636 aa. The simplest procedure is to select the 7 digit Gene ID. This brings up an Overview for the ORF, including a graphical display of the ORF showing its location in the phage genome. By selecting this graphical display, a drop-down menu will be displayed. If there are any CDs in the Orf, one of the choices will be Conserved Domains. By selecting this option, the ORF will be displayed in graphical form with the identity and position of the CDs detected in its sequence. In the example case of phi11_45, no CD is detected. This process is repeated for the next largest predicted protein product; in this case, it would be phi11_44, at 633 aa. There are two CDs present in this ORF, but neither belongs to the list shown in FIG. 1. In the example, the next ORF is phi11_49. This ORF turns out to have two CDs, CHAP and Lyz2, both of which are present in FIG. 1. Ideally, the process should be repeated for all the ORFs greater than 150 aa. Generally, a second ORF will yield at least one hit in FIG. 1. In the case of phi11, the ORF Phi11_53 is found to have the CHAP, Ami2 and SH3_5 domains.

After the complete list of predicted ORFs has been analyzed, in general two ORFs will be identified: the TAME and the lytic endolysin. Several criteria are applied to choose the TAME. First, a TAME will usually be the largest ORF containing a CD listed in FIG. 1. In the example of phage 11, the TAME is phi11_49, which is larger than the endolysin, phi11_53 (amidase). A second, confirmatory criteriaon may be available if phage tail proteins have been identified. The TAME will be grouped with the tail genes. In the case of phage 11, the TAME gene, phi11_49, is adjacent to the tail fiber gene, phi11_50, on the same (+) strand of the DNA, and downstream of other tail genes, including the tape measure gene, phi11_42. The endolysin (in this case, amidase; phi11_53), is usually adjacent to or close to the holin (in this case, phi11_52).

TAMEs in Current Staphylococcal Phages

The application of this procedure to the currently available Staphylococcal phages generated FIG. 1. In this FIGURE, the TAME candidate is listed (with its GI number in the far right column) for each bacteriophage; in the row pertaining to each phage, the CDs used to identify the TAME are listed.

Once cell binding domains and muralytic domains are identified, those of skill can, using the disclosure of this specification and standard molecular biology techniques, generate TAME-CBD proteins. Bactericidal function of large numbers of TAME-CBD proteins can be assayed using the assays described herein, e.g., lawn inhibition assays, zymogram assays, and colony forming unit (CFU) drop assays.

Many phage genomes are disclosed in publically available databases. The identification of conserved domains from Staphylococcal phages, both CBD and MD, that can be used in chermic TAME-CBD proteins can be extended by those of skill to identify conserved domains, both CBD and MD, from phages that infect other bacteria, e.g., phages that infect *Streptococcus* and *Anthrax* bacterial strains.

What is claimed is:

1. A chimeric polypeptide comprising
   (i) a first sequence having at least 90% identity to the sequence of amino acids 669-808 of SEQ ID NO:1, and
   (ii) a heterologous cell binding domain (CBD) that binds to a target bacterium, wherein the CBD has a sequence with at least 90% identity to a sequence selected from the group consisting of:
   amino acids 144-240 of SEQ ID NO:4;
   amino acids 149-257 of SEQ ID NO:8; and
   amino acids 144-243 of SEQ ID NO:12, and
   wherein the target bacterium exhibits reduced or no growth after being contacted with the chimeric polypeptide.

2. A pharmaceutical composition comprising the polypeptide of claim 1 and a pharmaceutically acceptable excipient.

3. The chimeric polypeptide of claim 2, wherein the CBD comprises a sequence with at least 90% identity to amino acids 144-240 of SEQ ID NO:4.

4. The chimeric polypeptide of claim 3, wherein the first sequence comprises the sequence of amino acids 669-808 of SEQ ID NO:1 and the CBD comprises the sequence of amino acids 144-240 of SEQ ID NO:4.

5. The chimeric polypeptide of claim 3, wherein the CBD comprises a sequence with at least 90% identity to amino acids 149-257 of SEQ ID NO:8.

6. The chimeric polypeptide of claim 5, wherein the first sequence comprises the sequence of amino acids 669-808 of SEQ ID NO:1 and the CBD comprises the sequence of amino acids 149-257 of SEQ ID NO:8.

7. The chimeric polypeptide of claim 4, wherein the CBD comprises a sequence with at least 90% identity to amino acids 144-243 of SEQ ID NO:12.

8. The chimeric polypeptide of claim 7, wherein the first sequence comprises the sequence of amino acids 669-808 of SEQ ID NO:1 and the CBD comprises the sequence of amino acids 144-243 of SEQ ID NO:12.

9. The chimeric polypeptide of claim 5, wherein the first sequence is a muralytic domain (MD).

10. The chimeric polypeptide of claim 6, wherein the first sequence has at least 90% identity to the sequence of amino acids 629-808 of SEQ ID NO: 1.

11. A chimeric polypeptide comprising
 (i) first sequence having at least 90% identity to the sequence of amino acids 669-808 of SEQ ID NO:1, and
 (ii) a second sequence having at least 90% identity to a sequence selected from the group consisting of:
  (a) amino acids 144-240 of SEQ ID NO:4,
  (b) amino acids 149-257 of SEQ ID NO:8, and
  (c) amino acids 144-243 of SEQ ID NO:12,
 wherein contact with the chimeric polypeptide reduces growth of a target bacterium.

12. The chimeric polypeptide of claim 11, wherein the first sequence comprises the sequence of amino acids 669-808 of SEQ ID NO:1 and the second sequence comprises the sequence of amino acids 144-240 of SEQ ID NO:4.

13. The chimeric polypeptide of claim 12, wherein the first sequence comprises the sequence of amino acids 669-808 of SEQ ID NO:1 and the second sequence comprises the sequence of amino acids 149-257 of SEQ ID NO:8.

14. The chimeric polypeptide of claim 13, wherein the first sequence comprises the sequence of amino acids 669-808 of SEQ ID NO:1 and the CBD comprises the sequence of amino acids 144-243 of SEQ ID NO:12.

15. The chimeric polypeptide of claim 14, wherein the first sequence has at least 90% identity to the sequence of amino acids 629-808 of SEQ ID NO:1.

\* \* \* \* \*